(12) United States Patent
Bauer et al.

(10) Patent No.: US 8,084,518 B2
(45) Date of Patent: Dec. 27, 2011

(54) ETHYLENEBIS(HYDROXYALKYLPHOSPHINIC ACID) AND SALTS THEREOF

(75) Inventors: Harald Bauer, Kerpen (DE); Werner Krause, Huerth (DE); Peter Staniek, Binzen (DE)

(73) Assignee: Clariant Finance (BVI) Limited, Tortola (VG)

( * ) Notice: Subject to any disclaimer, the term of this patent is extended or adjusted under 35 U.S.C. 154(b) by 29 days.

(21) Appl. No.: 12/444,794

(22) PCT Filed: Oct. 6, 2007

(86) PCT No.: PCT/EP2007/008692
§ 371 (c)(1),
(2), (4) Date: Apr. 8, 2009

(87) PCT Pub. No.: WO2008/043499
PCT Pub. Date: Apr. 17, 2008

(65) Prior Publication Data
US 2010/0093239 A1   Apr. 15, 2010

(30) Foreign Application Priority Data
Oct. 14, 2006   (DE) .................. 10 2006 048 698

(51) Int. Cl.
| C08L 63/00 | (2006.01) |
| C08K 5/53 | (2006.01) |
| C08K 5/5313 | (2006.01) |
| C07F 9/30 | (2006.01) |
| C07F 9/36 | (2006.01) |

(52) U.S. Cl. ........ 523/451; 524/121; 524/126; 524/133; 524/139; 524/147; 562/20; 562/23

(58) Field of Classification Search .............. None
See application file for complete search history.

(56) References Cited

U.S. PATENT DOCUMENTS

| | | | |
|---|---|---|---|
| 3,939,050 A * | 2/1976 | Kleiner et al. | .......... 204/157.64 |
| 4,001,352 A * | 1/1977 | Kleiner et al. | ............... 558/137 |
| 4,572,807 A | 2/1986 | Hagzle | |
| 6,569,974 B1 | 5/2003 | Sicken et al. | |
| 6,583,315 B2 * | 6/2003 | Sicken et al. | ................. 562/20 |
| 6,600,067 B2 | 7/2003 | Sicken et al. | |
| 6,600,068 B2 * | 7/2003 | Sicken et al. | ................. 562/20 |
| 6,727,335 B2 | 4/2004 | Sicken et al. | |
| 2002/0079480 A1 | 6/2002 | Sicken et al. | |
| 2003/0073865 A1 | 4/2003 | Sicken et al. | |
| 2003/0216533 A1 | 11/2003 | Sicken et al. | |

FOREIGN PATENT DOCUMENTS

| DE | 19912920 | 9/2000 |
| DE | 10065051 | 7/2002 |
| DE | 10065054 | 7/2002 |
| EP | 0061106 | 9/1982 |
| JP | 2004292532 | 10/2004 |
| WO | WO 01/57050 | 8/2001 |

OTHER PUBLICATIONS

PCT International Search Report for PCT/EP2007/008692, mailed Feb. 11, 2008.
English Abstract of JP 2004292532, Oct. 21, 2004.
Bruckmann et al. "Ethylene bis (phosphonic Acid)" XP 002466104, Acta Crystallographica, Section C: Crystal Structure Communications, C55 (4), 695-696 (1999).
Bellito el al. "Synthesis and Characterization of a new weak ferromognet." Fe (II) ethylene-bis (phosphonates); XP 002466105, Materials Reasearch Society Symposium Proceedings, 547 (Solid-State Chemistry of Inorganic Materials II), 487-492 (1999).
Podlahova et al, "Compounds Structurally Related to complexons XX Hydrolysis of ethylenediphospine tetraacetate anions," XP 002466106, 1984.
Collection of Czechoslovak Chemical Chemical Comnunications, 48 (6)1552-7 Coden; CCCCAK: ISSN 0366-547X, Database Beilstein [online] Beilstein Institute for Organic Chemistry, Frankfurt-Main DE, XP 002466107 (1983).
English translation of PCT International Report on Patentability for PCT/EP2007/008692, mailed May 14, 2009.
Database [online] Belstein Institute Zur Fuederung der Chemishen Wissenschaft, Frankfurt am Main DE; XP 002466108, Nifant'EV et al. J. Gen. Chem. USSR vol. 56 pp. 680-688 (1986).
English Translation of German Office Action for DE 102006048698. 6-44, Apr. 10, 2007.

* cited by examiner

Primary Examiner — Michael J Feely
(74) Attorney, Agent, or Firm — Anthony A. Bisulca

(57) ABSTRACT

The invention relates to an ethylenebis(hydroxyalkylphosphinic acid) and salts thereof. The acid has the general formula: A-P(O)(OX)—$CR^1R^2$—$CR^3R^4$—P(O)(OX)-A. Variable A is $CR^5R^6$—OH. Variables $R^1$, $R^2$, $R^3$, $R^4$, $R^5$, and $R^6$ are the same or different, and denote independently from each other H, $C_1$-$C_{20}$ alkyl, $C_6$-$C_{20}$ aryl, or $C_6$-$C_{20}$ aralkyl, so long as at least one of $R^1$ and $R^2$ is H and at least one of $R^3$ and $R^4$ is H. Variable X denotes H, an alkali metal, an element of main or transition group 2, an element of main or transition group 3, an element of main or transition group 4, an element of main or transition group 5, an element of transition group 6, an element of transition group 7, an element of transition group 8 and/or a nitrogen base. Also disclosed are a method for producing same and the use thereof.

11 Claims, No Drawings

ETHYLENEBIS(HYDROXYALKYLPHOSPHINIC ACID) AND SALTS THEREOF

The invention relates to ethylenediphosphinic acids, a process for preparing them and their use.

Ethylenediphosphinic acids are fundamentally known from the prior art. Thus, DE-A-199 12 920 and WO-A-0 157 050 describe phosphinic acids of the type H—P(O)(OX)—[CH$_2$CH$_2$—P(O)(OX)]$_n$H where X is H, metal or an alkyl group and n is greater than 1. These phosphinic acids are oligomeric or polymeric. They are prepared by processes which produce telomers but do not make it possible to obtain phosphinic acids having a specific chain length.

It is therefore an object of the present invention to provide ethylenediphosphinic acids which in each case have a specific chain length and can thus be "tailored" to their respective uses.

The invention accordingly provides ethylenediphosphinic acids and salts thereof having the formula (I)

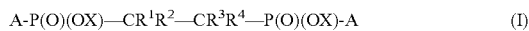

A-P(O)(OX)—CR$^1$R$^2$—CR$^3$R$^4$—P(O)(OX)-A  (I)

where A is H and/or CR$^5$R$^6$—OH,

R$^1$, R$^2$, R$^3$, R$^4$, R$^5$, R$^6$ are identical or different and are each, independently of one another, H, C$_1$-C$_{20}$-alkyl, C$_6$-C$_{20}$-aryl or C$_6$-C$_{20}$-aralkyl and X is H, an alkali metal, an element of main or transition group 2, an element of main or transition group 3, an element of main or transition group 4, an element of main or transition group 5, an element of transition group 6, an element of transition group 7, an element of transition group 8 and/or a nitrogen base.

Preference is given to R$^1$, R$^2$, R$^3$, R$^4$, R$^5$, R$^6$ being identical or different and each being, independently of one another, H, methyl, ethyl, n-propyl, i-propyl, n-butyl, tert-butyl, n-pentyl or phenyl.

Preference is given to A being H and X being Li, Na, K; Mg, Ca, Zn, Sr; Al, Ce, La; Ge, Sn, Pb, Ti, Zr; Sb, Bi; Cr, Mo, W; Mn; Fe, Co or Ni.

Particularly preference is given to A being H and X being H, Na, Al, Zn, Ca, Mg, Ti or melamine.

The invention also provides a process (1) for preparing ethylenediphosphinic acids and salts thereof having the formula (I)

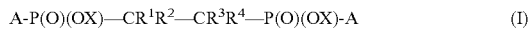

A-P(O)(OX)—CR$^1$R$^2$—CR$^3$R$^4$—P(O)(OX)-A  (I)

where A is H and/or CR$^5$R$^6$—OH,

R$^1$, R$^2$, R$^3$, R$^4$, R$^5$, R$^6$ are identical or different and are each, independently of one another, H, C$_1$-C$_{20}$-alkyl, C$_6$-C$_{20}$-aryl or C$_6$-C$_{20}$-aralkyl and X is H or an alkali metal, wherein a) a monophosphinic acid adduct of the formula (II)

H—P(O)(OX)-A  (II)

is reacted with acetylene and b) if desired, the resulting ethylenediphosphinic acid of the type A-P(O)(OX)—CR$^1$R$^2$—CR$^3$R$^4$—P(O)(OX)-A is separated off from by-products.

The invention also relates to a process (2) for preparing ethylenebis(hydroxyalkylphosphinic acid) salts or ethylenediphosphinic acid salts of the type A-P(O)(OX)—CR$^1$R$^2$—CR$^3$R$^4$—P(O)(OX)-A, where A, R$^1$, R$^2$, R$^3$, R$^4$, R$^5$ and R$^6$ are as defined in claim 1 and X is an alkali metal, an element of main group or transition group 2, an element of main or transition group 3, an element of main or transition group 4, an element of main or transition group 5, an element of transition group 6, an element of transition group 7, an element of transition group 8 and/or a nitrogen base, wherein an ethylenebis(hydroxyalkylphosphinic acid) or ethylenediphosphinic acid of the type A-P(O)(OX)—CR$^1$R$^2$—CR$^3$R$^4$—P(O)(OX)-A, where A, R$^1$, R$^2$, R$^3$, R$^4$, R$^5$ and R$^6$ are as defined in claim 1 and X is H, is reacted in a solvent system with a reactant I which is a compound of an alkali metal, of an element of main or transition group 2, of an element of main or transition group 3, of an element of main or transition group 4, of an element of main or transition group 5, of an element of transition group 6, of an element of transition group 7, of an element of transition group 8 and/or a nitrogen base.

The invention also provides a process (3) for preparing ethylenebis(hydroxyalkylphosphinic acid) salts or ethylenediphosphinic acid salts of the type

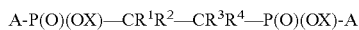

A-P(O)(OX)—CR$^1$R$^2$—CR$^3$R$^4$—P(O)(OX)-A where A, R$^1$, R$^2$, R$^3$, R$^4$, R$^5$ and R$^6$ are as defined in claim 1 and X is an element of main group or transition group 2, an element of main or transition group 3, an element of main or transition group 4, an element of main or transition group 5, an element of transition group 6, an element of transition group 7, an element of transition group 8 and/or a nitrogen base, wherein ethylenebis(hydroxyalkylphosphinic acid) or ethylenediphosphinic acid of the type

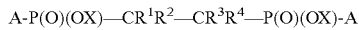

A-P(O)(OX)—CR$^1$R$^2$—CR$^3$R$^4$—P(O)(OX)-A where A, R$^1$, R$^2$, R$^3$, R$^4$, R$^5$ and R$^6$ are as defined in claim 1 and X is an alkali metal, is reacted in a solvent system with a reactant II to form another metal salt (not an alkali metal salt).

The reactant II is preferably a borate, carbonate, hydroxocarbonate, hydroxocarbonate hydrate, mixed hydroxocarbonate, mixed hydroxocarbonate hydrate, phosphate, sulfate, sulfate hydrate, hydroxosulfate hydrate, mixed hydroxosulfate hydrate, oxysulfate, acetate, nitrate, fluoride, fluoride hydrate, chloride, chloride hydrate, oxychloride, bromide, iodide, iodide hydrate, carboxylic acid derivative and/or alkoxide.

The invention also provides a process (4) for preparing ethylenediphosphinic acid salts of the type

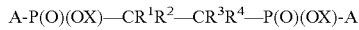

A-P(O)(OX)—CR$^1$R$^2$—CR$^3$R$^4$—P(O)(OX)-A where R$^1$, R$^2$, R$^3$, R$^4$, R$^5$ and R$^6$ are as defined in claim 1 and A is H and X is H, an alkali metal, an element of main or transition group 2, an element of main or transition group 3, an element of main or transition group 4, an element of main or transition group 5, an element of transition group 6, an element of transition group 7, an element of transition group 8 and/or a nitrogen base, wherein an ethylenebis(hydroxyalkylphosphinic acid) of the type

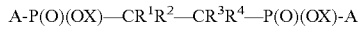

A-P(O)(OX)—CR$^1$R$^2$—CR$^3$R$^4$—P(O)(OX)-A where R$^1$, R$^2$, R$^3$, R$^4$, R$^5$ and R$^6$ are as defined in claim 1 and A is CR$^5$R$^6$—OH and X is H, an alkali metal, an element of main or transition group 2, an element of main or transition group 3, an element of main or transition group 4, an element of main or transition group 5, an element of transition group 6, an element of transition group 7, an element of transition group 8 and/or a nitrogen base, is heated.

In the abovementioned process, the ethylenebis(hydroxyalkylphosphinic acid) is preferably heated to from 20 to 300° C., particularly preferably from 50 to 200° C.

Heating is preferably carried out in a protic acid which is a mineral acid (hydrochloric acid, sulfuric acid, phosphoric acid), carboxylic acid (formic acid, acetic acid, polymeric carboxylic acid), sulfonic acid, phosphonic acid, organically crosslinked carboxylic, sulfonic, phosphonic acid or a mixture thereof.

The invention also provides for the use of ethylenediphosphinic acids as claimed in at least one of claims 1 to 5 as flame retardants, in particular flame retardants for clear coatings and intumescent coatings, flame retardants for wood and other cellulose-containing products, as reactive and/or non-reactive flame retardants for polymers, for producing flame-retarded polymer molding compositions, for producing flame-retarded polymer moldings and/or for the flame-resistant treatment of polyesters and cellulose pure and mixed woven fabrics by impregnation.

Preference is given to the use of the inventive ethylenediphosphinic acid and/or salt thereof as binder, e.g. for foundry compositions, mold sands.

Preference is given to the use of the inventive ethylenediphosphinic acid and/or salt thereof as crosslinker or accelerator in the curing of epoxy resins, polyurethanes, unsaturated polyester resins.

Preference is given to the use of the inventive ethylenediphosphinic acid and/or salt thereof as polymer stabilizer, e.g. as light stabilizer, free-radical scavenger and/or heat stabilizer for woven cotton fabrics, polymer fibers, plastics.

Preference is given to the use of the inventive ethylenediphosphinic acid and/or salt thereof as crop protection agent, e.g. as plant growth regulator, as herbicide, pesticide or fungicide.

Preference is given to the use of the inventive ethylenediphosphinic acid and/or salt thereof as therapeutic agent or additive in therapeutic agents for human beings and animals, e.g. as enzyme modulator or for the stimulation of tissue growth.

Preference is given to the use of the inventive ethylenediphosphinic acid and/or salt thereof as sequestering agent, e.g. for the control of deposits in industrial water piping systems, in mineral oil recovery and in metal treatment agents.

Preference is given to the use of the inventive ethylenediphosphinic acid and/or salt thereof as mineral oil additive, e.g. as antioxidant and for increasing the octane number.

Preference is given to the use of the inventive ethylenediphosphinic acid and/or salt thereof as corrosion inhibitor.

Preference is given to the use of the inventive ethylenediphosphinic acid and/or salt thereof in laundry detergent and cleaner applications, e.g. as decolorizing agent.

Preference is given to the use of the inventive ethylenediphosphinic acid and/or salt thereof in electronics applications, e.g. in polyelectrolytes for capacitors, batteries and accumulators, and as free-radical scavenger in photosensitive layers.

Preference is given to the use of the inventive ethylenediphosphinic acid and/or salt thereof as aldehyde scavenger. It has surprisingly been found that the ethylenediphosphinic acids of the invention can be used for reducing the liberation of aldehyde. Preferred aldehydes are formaldehyde and acetaldehyde.

Formaldehyde scavengers are preferably used in adhesives, shaped bodies, e.g. in building applications, the automobile, shipbuilding, aircraft and spaceflight industries, and for electrical engineering, etc.

The invention also provides a flame-retardant thermoplastic polymer molding composition containing from 0.5 to 45% by weight of ethylenediphosphinic acid as claimed in at least one of claims 1 to 5 and from 0.5 to 99.5% by weight of thermoplastic polymer or mixture thereof, with the sum of the components being 100% by weight.

The invention also provides a flame-retardant thermoset composition containing from 0.1 to 45% by weight of ethylenediphosphinic acid as claimed in at least one of claims 1 to 5, from 40 to 89.9% by weight of unsaturated polyester and from 10 to 60% by weight of vinyl monomer, with the sum of the components being 100% by weight.

The invention also provides an epoxy resin which has been treated to make it flame resistant and contains from 0.5 to 50% by weight of ethylenediphosphinic acid as claimed in at least one of claims 1 to 5, from 5 to 99.5% by weight of an epoxy resin and from 0 to 20% by weight of a hardener, with the sum of the components being 100% by weight.

Preferred ethylenediphosphinic acids correspond to the formula

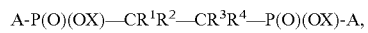

where $R^1$, $R^2$, $R^3$, $R^4$ are each H and A is H, so that when X is H, the resulting ethylenediphosphinic acid has the formula

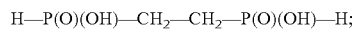

and when X is an alkali metal, preferably Na, the resulting ethylenediphosphinic acid salt has the formula

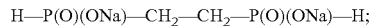

and when X is aluminum, i.e. $Al_{1/3}$, the resulting ethylenediphosphinic acid salt has the formula

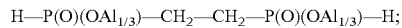

and when X is melamine, i.e. Mel, the resulting ethylenediphosphinic acid melamine salt has the formula

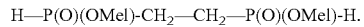

Preferred ethylenediphosphinic acids also correspond to the formula

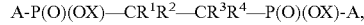

where $R^1$, $R^2$, $R^3$, $R^4$ are each H and A is $CR^5R^6$—OH, where $R^5$, $R^6$ are each H, so that when X is H, the resulting ethylenediphosphinic acid has the formula

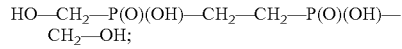

and when X is an alkali metal, preferably Na, the resulting ethylenediphosphinic acid salt has the formula

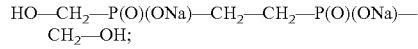

and when X is Al, i.e. $Al_{1/3}$, the resulting ethylenediphosphinic acid salt has the formula

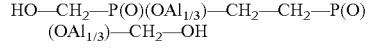

and when X is melamine, i.e. Mel, the resulting ethylenediphosphinic acid melamine salt has the formula

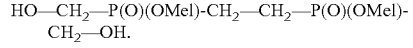

Preferred ethylenediphosphinic acids also correspond to the formula

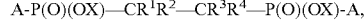

where $R^1$, $R^2$, $R^3$, $R^4$ are each H and A is $CR^5R^6$—OH, where $R^5$ is $CH_3$ and $R^6$ is H, so that when X is H, the resulting ethylenediphosphinic acid has the formula

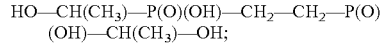

and when X is an alkali metal, preferably Na, the resulting ethylenediphosphinic acid salt has the formula

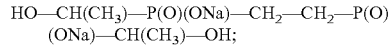

and when X is zinc, i.e. $Zn_{1/2}$, the resulting ethylenediphosphinic acid salt has the formula $$HO-CH(CH_3)-P(O)(OZn_{1/2})-CH_2-CH_2-P(O)(OZn_{1/2})-CH(CH_3)-OH;$$

and when X is ammonium, i.e. $NH_4$, the resulting ethylenediphosphinic acid ammonium salt has the formula $$HO-CH(CH_3)-P(O)(ONH_4)-CH_2-CH_2-P(O)(ONH_4)-CH(CH_3)-OH.$$

Preferred ethylenediphosphinic acids also correspond to the formula $$A-P(O)(OX)-CR^1R^2-CR^3R^4-P(O)(OX)-A,$$

where $R^1$, $R^2$, $R^3$, $R^4$ are each H and A is $CR^5R^6-OH$, where $R^5$ is phenyl and $R^6$ is H, so that when X is H, the resulting ethylenediphosphinic acid has the formula $$HO-CH(phenyl)-P(O)(OH)-CH_2-CH_2-P(O)(OH)-CH(phenyl)-OH;$$

and when X is an alkali metal, preferably Na, the resulting ethylenediphosphinic acid salt has the formula $$HO-CH(phenyl)-P(O)(ONa)-CH_2-CH_2-P(O)(ONa)-CH(phenyl)-OH;$$

and when X is titanium, i.e. $Ti_{1/3}$, the resulting ethylenediphosphinic acid salt has the formula $$HO-CH(phenyl)-P(O)(OTi_{1/3})-CH_2-CH_2-P(O)(ONa_{1/3})-CH(phenyl)-OH;$$

and when X is melamine, i.e. Mel, the resulting ethylenediphosphinic acid melamine salt has the formula $$HO-CH(phenyl)-P(O)(OMel)-CH_2-CH_2-P(O)(OMel)-CH(phenyl)-OH.$$

Preferred ethylenediphosphinic acids also correspond to the formula $$A-P(O)(OX)-CR^1R^2-CR^3R^4-P(O)(OX)-A,$$

where $R^1$, $R^2$, $R^3$, $R^4$ are each H and A is $CR^5R^6-OH$, where $R^5$, $R^6$ are each $CH_3$, so that when X is H, the resulting ethylenediphosphinic acid has the formula $$HO-C(CH_3)_2-P(O)(OH)-CH_2-CH_2-P(O)(OH)-C(CH_3)_2-OH;$$

and when X is an alkali metal, preferably Na, the resulting ethylenediphosphinic acid salt has the formula $$HO-C(CH_3)_2-P(O)(ONa)-CH_2-CH_2-P(O)(ONa)-C(CH_3)_2-OH;$$

and when X is magnesium, i.e. $Mg_{1/2}$, the resulting ethylenediphosphinic acid salt has the formula $$HO-C(CH_3)_2-P(O)(OMg_{1/2})-CH_2-CH_2-P(O)(OMg_{1/2})-C(CH_3)_2-OH;$$

and when X is melamine, i.e. Mel, the resulting ethylenediphosphinic acid melamine salt has the formula $$HO-C(CH_3)_2-P(O)(OMel)-CH_2-CH_2-P(O)(OMel)-C(CH_3)_2-OH.$$

Preferred ethylenediphosphinic acids also correspond to the formula $$A-P(O)(OX)-CR^1R^2-CR^3R^4-P(O)(OX)-A,$$

where $R^1$, $R^2$, $R^3$, $R^4$ are each H and A is $CR^5R^6-OH$, where $R^5$ is $CH_3$, $R^6$ is $C_2H_5$, so that when X is H, the resulting ethylenediphosphinic acid has the formula $$HO-C(CH_3)(C_2H_5)-P(O)(OH)-CH_2-CH_2-P(O)(OH)-C(CH_3)(C_2H_5)-OH;$$

and when X is an alkali metal, preferably Na, the resulting ethylenediphosphinic acid salt has the formula $$HO-C(CH_3)(C_2H_5)-P(O)(OK)-CH_2-CH_2-P(O)(OK)-C(CH_3)(C_2H_5)-OH;$$

and when X is aluminum, i.e. $Al_{1/3}$, the resulting ethylenediphosphinic acid salt has the formula $$HO-C(CH_3)(C_2H_5)-P(O)(OAl_{1/3})-CH_2-CH_2-P(O)(OAl_{1/3})-C(CH_3)(C_2H_5)-OH;$$

and when X is ammonium, i.e. $NH_4$, the resulting ethylenediphosphinic acid ammonium salt has the formula $$HO-C(CH_3)(C_2H_5)-P(O)(ONH_4)-CH_2-CH_2-P(O)(ONH_4)-C(CH_3)(C_2H_5)-OH.$$

Preferred ethylenediphosphinic acids also correspond to the formula $$A-P(O)(OX)-CR^1R^2-CR^3R^4-P(O)(OX)-A,$$

where $R^1$, $R^2$, $R^3$, $R^4$ are each H and A is $CR^5R^6-OH$, where $R^5$ is $CH_3$, $R^6$ is phenyl, so that when X is H, the resulting ethylenediphosphinic acid has the formula $$HO-C(CH_3)(phenyl)-P(O)(OH)-CH_2-CH_2-P(O)(OH)-C(CH_3)(phenyl)-OH;$$

and when X is an alkali metal, preferably Li, the resulting ethylenediphosphinic acid salt has the formula $$HO-C(CH_3)(phenyl)-P(O)(OH)-CH_2-CH_2-P(O)(OH)-C(CH_3)(phenyl)-OH;$$

and when X is zinc i.e. $Zn_{1/2}$, the resulting ethylenediphosphinic acid salt has the formula $$HO-C(CH_3)(phenyl)-P(O)(OZn_{1/2})-CH_2-CH_2-P(O)(OZn_{1/2})-C(CH_3)(phenyl)-OH;$$

and when X is melamine, i.e. Mel, the resulting ethylenediphosphinic acid melamine salt has the formula $$HO-C(CH_3)(phenyl)-P(O)(OMel)-CH_2-CH_2-P(O)(OMel)-C(CH_3)(phenyl)-OH.$$

Preferred ethylenediphosphinic acids also correspond to the formula $$A-P(O)(OX)-CR^1R^2-CR^3R^4-P(O)(OX)-A,$$

where $R^1$ is methyl, $R^2$, $R^3$, $R^4$ are each H and A is H, so that when X is H, the resulting ethylenediphosphinic acid has the formula $$H-P(O)(OH)-CH(CH_3)-CH_2-P(O)(OH)-H;$$

and when X is an alkali metal, preferably Na, the resulting ethylenediphosphinic acid salt has the formula $$H-P(O)(ONa)-CH(CH_3)-CH_2-P(O)(ONa)-H;$$

and when X is Al, i.e. $Al_{1/3}$, the resulting ethylenediphosphinic acid salt has the formula $$H-P(O)(OAl_{1/3})-CH(CH_3)-CH_2-P(O)(OAl_{1/3})-H;$$

and when X is melamine, i.e. Mel, the resulting ethylenediphosphinic acid melamine salt has the formula $$H-P(O)(OMel)-CH(CH_3)-CH_2-P(O)(OMel)-H.$$

Preferred ethylenediphosphinic acids also correspond to the formula $$A-P(O)(OX)-CR^1R^2-CR^3R^4-P(O)(OX)-A,$$

where $R^1$ is methyl, $R^2$, $R^3$, $R^4$ are each H and A is $CR^5R^6-OH$, where $R^5$, $R^6$ are each $CH_3$, so that when X is H, the resulting ethylenediphosphinic acid has the formula $$HO-C(CH_3)_2-P(O)(OH)-CH(CH_3)-CH_2-P(O)(OH)-C(CH_3)_2-OH;$$

and when X is an alkali metal, preferably K, the resulting ethylenediphosphinic acid salt has the formula

HO—C(CH$_3$)$_2$—P(O)(OK)—CH(CH$_3$)—CH$_2$—P(O)(OK)—C(CH$_3$)$_2$—OH;

and when X is magnesium, i.e. Mg$_{1/2}$, the resulting ethylenediphosphinic acid salt has the formula HO—C(CH$_3$)$_2$—P(O)(OMg$_{1/2}$)—CH(CH$_3$)—CH$_2$—P(O)(OMg$_{1/2}$)—C(CH$_3$)$_2$OH;

and when X is ammonium, i.e. NH$_4$, the resulting ethylenediphosphinic acid ammonium salt has the formula

HO—C(CH$_3$)$_2$—P(O)(ONH$_4$)—CH(CH$_3$)—CH$_2$—P(O)(ONH$_4$)—C(CH$_3$)$_2$—OH.

Preferred ethylenediphosphinic acids also correspond to the formula

A-P(O)(OX)—CR$^1$R$^2$—CR$^3$R$^4$—P(O)(OX)-A, where R$^1$ is phenyl, R$^2$, R$^3$, R$^4$ are each H and A is H, so that when X is H, the resulting ethylenediphosphinic acid has the formula H—P(O)(OH)—CH(phenyl)-CH$_2$—P(O)(OH)—H;

and when X is an alkali metal, preferably Na, the resulting ethylenediphosphinic acid salt has the formula H—P(O)(ONa)—CH(phenyl)-CH$_2$—P(O)(ONa)—H;

and when X is Al, i.e. Al$_{1/3}$, the resulting ethylenediphosphinic acid salt has the formula H—P(O)(OAl$_{1/3}$)—CH(phenyl)-CH$_2$—P(O)(OAl$_{1/3}$)—H;

and when X is melamine, i.e. Mel, the resulting ethylenediphosphinic acid melamine salt has the formula H—P(O)(OMel)-CH(phenyl)-CH$_2$—P(O)(OMel)-H.

Preferred ethylenediphosphinic acids also correspond to the formula

A-P(O)(OX)—CR$^1$R$^2$—CR$^3$R$^4$—P(O)(OX)-A, where R$^1$ is phenyl, R$^2$, R$^3$, R$^4$ are each H and A is CR$^5$R$^6$—OH, where R$^5$, R$^6$ are each CH$_3$, so that when X is H, the resulting ethylenediphosphinic acid has the formula HO—C(CH$_3$)$_2$—P(O)(OH)—CH(phenyl)-CH$_2$—P(O)(OH)—C(CH$_3$)$_2$—OH;

and when X is an alkali metal, preferably K, the resulting ethylenediphosphinic acid salt has the formula HO—C(CH$_3$)$_2$—P(O)(OK)—CH(phenyl)-CH$_2$—P(O)(OK)—C(CH$_3$)$_2$—OH;

and when X is titanium, i.e. Ti$_{1/3}$, the resulting ethylenediphosphinic acid salt has the formula HO—C(CH$_3$)$_2$—P(O)(OTi$_{1/3}$)—CH(phenyl)-CH$_2$—P(O)(OTi$_{1/3}$)—C(CH$_3$)$_2$—OH;

and when X is ammonium, i.e. NH$_4$, the resulting ethylenediphosphinic acid ammonium salt has the formula HO—C(CH$_3$)$_2$—P(O)(ONH$_4$)—CH(phenyl)-CH$_2$—P(O)(ONH$_4$)—C(CH$_3$)$_2$—OH.

Preferred nitrogen bases are ammonium, substituted ammonium, ethylenediamine, hydroxylamine, urea, N-alicyclic compounds such as pyrrolidine, piperidine, imidazolidine, piperazine, N-aromatic compounds such as heteroaromatic ring compounds such as pyrrole, pyridine, imidazole, pyrazine, substituted urea derivatives (e.g. dimethylurea, N,N'-diphenylurea, benzylurea, acetyleneurea, tetramethylurea), thiourea, guanidine, substituted guanidine derivatives (e.g. alkylguanidine, arylguanidine, diphenylguanidine), biguanide, melamine, substituted melamine derivatives (e.g. ethylenedimelamine), condensation products of melamine and more highly condensed compounds thereof, e.g. melem, melam or melon, melamine-phenol systems, benzoguanamine, acetoguanamine, urethanes, cyanamide, dicyandiamide, aniline, sulfonamide, biuret, allantoin, tolyltriazole, benzotriazole, 2-amino-4-methylpyrimidine, hydantoin, substituted hydantoin derivatives (e.g. 5,5-diphenylhydantoin), malonamide amidine, ethylenebis-5-triazone, glycine anhydride and any mixtures thereof.

Preferred alkali metals are sodium, potassium.

The reaction of the monophosphinic acid adduct with acetylene in process (1) preferably takes place
a) in the presence of a solvent and a free-radical initiator,
b) by placing monophosphinic acid adduct and solvent in a reaction vessel and secondly feeding in acetylene and initiator (if desired in a solvent),
c) by placing monophosphinic acid adduct, acetylene and solvent in a reaction vessel and feeding in initiator (if desired in a solvent),
d) by placing monophosphinic acid adduct, solvent and initiator in a reaction vessel and feeding in acetylene (if desired in a solvent),
e) by placing monophosphinic acid adduct, acetylene, solvent and initiator in a reaction vessel.

The product is preferably separated off in process (1) by
a) solid-liquid separation (e.g. filtration, centrifugation, allowing to settle),
b) liquid-liquid separation (e.g. extraction, etc).

Preferred adducts for process (1) are those with aldehydes and/or ketones.

Preferred aldehydes for process (1) are aliphatic aldehydes (formaldehyde, acetaldehyde, propionaldehyde, butyraldehyde, valeraldehyde, caproaldehyde, acrolein, crotonaldehyde, propargyl aldehyde) and/or aromatic aldehydes (benzaldehyde, p-tolualdehyde, anisaldehyde or salicylaldehyde, vanillin).

Preferred ketones for process (1) are aliphatic ketones (acetone, methyl ethyl ketone, chloroacetone, methyl vinyl ketone, mesityl oxide, phorone) or aromatic ketones (acetophenone, benzophenone).

Preferred aldehydes are aliphatic aldehydecarboxylic acids (glyoxylic acid).

Preferred ketones are aliphatic ketocarboxylic acids (pyruvic acid, acetoacetic acid, levulinic acid).

Preferred aldehydes are aliphatic hydroxyaldehydes (glycolaldehyde, glyceraldehyde).

Preferred aldehydes are aliphatic hydroxyketones (acetol, acetoin, dihydroxyacetone).

Preferred aldehydes are aliphatic dialdehydes (glyoxal, malonaldehyde, succinaldehyde).

Preferred aldehydes are ketoaldehydes (methylglyoxal).

Preferred ketones are diketones (diacetyl, acetylacetone, acetonylacetone).

Suitable free-radical initiators for process (1) are in principle all systems which generate free radicals. The addition reaction of the olefin can be initiated by means of an anionic initiator, a free-radical initiator or photochemically.

Particularly preferred free-radical initiators are peroxo compounds such as peroxomonosulfuric acid, potassium persulfate (potassium peroxomonosulfate), Caroat™, Oxone™, peroxodisulfuric acid, potassium persulfate (potassium peroxodisulfate), sodium persulfate (sodium peroxodisulfate), ammonium persulfate (ammonium peroxodisulfate).

Particular preference is given to compounds which can form peroxides in the solvent system, e.g. sodium peroxide, sodium peroxide diperoxohydrate, sodium peroxide diperoxohydrate hydrate, sodium peroxide dihydrate, sodium peroxide octahydrate, lithium peroxide, lithium peroxide monoperoxohydrate trihydrate, calcium peroxide, strontium peroxide, barium peroxide, magnesium peroxide, zinc peroxide, potassium hyperoxide, potassium peroxide diperoxohydrate, sodium peroxoborate tetrahydrate, sodium peroxoborate trihydrate, sodium peroxoborate monohydrate, anhydrous sodium peroxoborate, potassium peroxoborate peroxohydrate, magnesium peroxoborate, calcium peroxoborate, barium peroxoborate, strontium peroxoborate, potassium peroxoborate, peroxomonophosphoric acid, peroxodiphosphoric acid, potassium peroxodiphosphate, ammonium peroxodiphosphate, potassium ammonium peroxodiphosphate (double salt), sodium carbonate peroxohydrate, urea peroxohydrate, ammonium oxalate peroxide, barium peroxide peroxohydrate, calcium hydrogen peroxide, calcium peroxide peroxohydrate, ammonium triphosphate diperoxophosphate hydrate, potassium fluoride peroxohydrate, potassium fluoride triperoxohydrate, potassium fluoride diperoxohydrate, sodium pyrophosphate diperoxohydrate, sodium pyrophosphate diperoxohydrate octahydrate, potassium acetate peroxohydrate, sodium phosphate peroxohydrate, sodium silicate peroxohydrate.

Particular preference is given to hydrogen peroxide, performic acid, peracetic acid, benzoyl peroxide, di-t-butyl peroxide, dicumyl peroxide, 2,4-dichlorobenzoyl peroxide, decanoyl peroxide, lauryl peroxide, cumene hydroperoxide, pinene hydroperoxide, p-methane hydroperoxide, t-butyl hydroperoxide, acetylacetone peroxide, methyl ethyl ketone peroxide, succinic peroxide, dicetyl peroxydicarbonate, t-butyl peroxyacetate, t-butyl peroxymaleate, t-butyl peroxybenzoate, acetyl cyclohexylsulfonyl peroxide.

Preference is given to using water-soluble azo compounds as free-radical initiators.

Preference is also given to azo initiators such as 2-t-butylazo-2-cyanopropane, dimethyl azodiisobutyrate, azobisisobutyronitrile, 2-t-butylazo-1-cyanocyclohexane, 1-t-amylazo-1-cyanocyclohexane. Preference is also given to alkyl perketals such as 2,2-bis(t-butylperoxy)butane, ethyl 3,3-bis(t-butylperoxy)butyrate, 1,1-di(t-butylperoxy)cyclohexane.

Particular preference is given to azo initiators such as ® VAZO 52, ® VAZO 64 (AIBN), ® VAZO 67, ® VAZO 88, ® VAZO 44, ® VAZO 56, ® VAZO 68 from Dupont-Biesteritz, V-70 2,2'-azobis(4-methoxy-2,4-dimethylvaleronitrile), V-65 2,2'-azobis(2,4-dimethylvaleronitrile), V-601 dimethyl 2,2'-azobis(2-methylpropionate), V-59 2,2'-azobis(2-methylbutyronitrile), V-40, VF-096 1,1'-azobis(cyclohexane-1-carbonitrile), V-30 1-[(cyano-1-methylethyl)azo]formamide, VAm-110 2,2'-azobis(N-butyl-2-methylpropionamide), Am-111 2,2'-azobis(N-cyclohexyl-2-methylpropionamide), VA-041 2,2'-azobis[2-(5-methyl-2-imidazolin-2-yl)propane] dihydrochloride, VA-044 2,2'-azobis[2-(2-imidazolin-2-yl)propane]dihydrochloride, VA-046B 2,2'-azobis[2-(2-imidazolin-2-yl)propane disulfate dihydrate, V-50 2,2'-azobis(2-amidinopropane)hydrochloride, VA-057 2,2'-azobis-[N-(2-carboxyethyl)-2-methylpropionamidine]tetrahydrate, VA-058 2,2'-azobis[2-(3,4,5,6-tetrahydropyrimidin-2-yl)propane]dihydrochloride, VA-060 2,2'-azobis{2-[1-(2-hydroxyethyl)-2-imidazolin-2-yl]propane}dihydrochloride, VA-061, 2,2'-azobis[2-(2-imidazolin-2-yl)propane], VA-080 2,2'-azobis{2-methyl-N-[1,1-bis(hydroxymethyl)-2-hydroxyethyl]propionamide, VA-085 2,2'-azobis{2-methyl-N-(2-(1-hydroxybutyl)]propionamide, VA-086 2,2'-azobis[2-methyl-N-(2-hydroxyethyl)propionamide] from Wako Chemicals.

The preparation in process (1) can be carried out using a solvent. Solvents which are suitable according to the invention are preferably water, alcohols such as methanol, ethanol, isopropanol, n-propanol, n-butanol, isobutanol, t-butanol, n-amyl alcohol, isoamyl alcohol, t-amyl alcohol, n-hexanol, n-octanol, isooctanol, n-tridecanol, benzyl alcohol, etc. Preference is also given to glycols such as ethylene glycol, 1,2-propanediol, 1,3-propanediol, 1,3-butanediol, 1,4-butanediol, diethylene glycol, etc; aliphatic hydrocarbons such as pentane, hexane, heptane, octane and petroleum ether, petroleum benzene, kerosene, petroleum, paraffin oil, etc; aromatic hydrocarbons such as benzene, toluene, xylene, mesitylene, ethylbenzene, diethylbenzene, etc; halogenated hydrocarbons such as methylene chloride, chloroform, 1,2-dichloroethane, chlorobenzene, carbon tetrachloride, tetrabromoethylene, etc; alicyclic hydrocarbons such as cyclopentane, cyclohexane and methylcyclohexane, etc; ethers such as anisole (methyl phenyl ether), t-butyl methyl ether, dibenzyl ether, diethyl ether, dioxane, diphenyl ether, methyl vinyl ether, tetrahydrofuran, triisopropyl ether, etc; glycol ethers such as diethylene glycol diethyl ether, diethylene glycol dimethyl ether (diglyme), diethylene glycol monobutyl ether, diethylene glycol monomethyl ether, 1,2-dimethoxyethane (DME, monoglyme), ethylene glycol monobutyl ether, triethylene glycol dimethyl ether (triglyme), triethylene glycol monomethyl ether, etc; ketones such as acetone, diisobutyl ketone, methyl n-propyl ketone; methyl ethyl ketone, methyl isobutyl ketone, etc; esters such as methyl formate, methyl acetate, ethyl acetate, n-propyl acetate and n-butyl acetate, etc; carboxylic acids such as formic acid, acetic acid, propionic acid, butyric acid, etc. One or more of these compounds can be used either or alone or in combination.

According to the invention, preference is given to a weight ratio of solvent to monophosphinic acid adduct in process (1) of from 100:1 to 1:100, particularly preferably from 10:1 to 1:10.

According to the invention, preference is given to a molar ratio of initiator to monophosphinic acid adduct in process (1) of from 1:1 to 1:1000, particularly preferably from 1:2 to 1:100.

According to the invention, preference is given to a molar ratio of acetylene to monophosphinic acid adduct in process (1) of from 100:1 to 1:100, particularly preferably from 5:1 to 1:5.

According to the invention, preference is given to a reaction time of from 0.1 to 100 h, particularly from 1 to 10 h, in process (1).

According to the invention, the phosphinic acid of the type

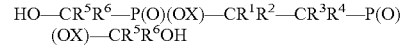
HO—CR$^5$R$^6$—P(O)(OX)—CR$^1$R$^2$—CR$^3$R$^4$—P(O)(OX)—CR$^5$R$^6$OH is preferably purified.

Preferred purification methods in process (1) are
a) recrystallization from a solvent according to the invention and solid-liquid separation,
b) digestion with a solvent according to the invention and solid-liquid separation.

The preferred radio of solvent to phosphinic acid of the type HO—CR$^5$R$^6$—P(O)(OX)—CR$^1$R$^2$—CR$^3$R$^4$—P(O)(OX)—CR$^5$R$^6$OH for the preferred purification method in process (1) is from 1000:1 to 4:1, particularly preferably from 100:1 to 1:1.

The preferred temperature for the purification process in process (1) is from 20 to 200° C., particularly preferably from 50 to 150° C.

The preferred pressure for the purification process in process (1) is from 10 to 100 000 000 Pa.

Preference is given to a purity after process (1) of greater than 90%, particularly preferably greater than 95%.

The invention also provides processes for preparing ethylenebis(hydroxyalkylphosphinic acid) salts and ethylenediphosphinic acid salts, in which the acids are converted into aluminum salts or the alkali metal salts are converted into aluminum salts.

According to the invention, preference is given to a process (2) in which an ethylenebis(hydroxyalkylphosphinic acid) or ethylenediphosphinic acid according to the invention in which X is H is reacted in a suitable solvent system with a reactant A.

In a process (3), the inventive salt of the ethylenebis(hydroxyalkylphosphinic acid) or ethylenediphosphinic acid according to the invention in which X is an alkali metal can preferably be converted in a suitable solvent into another metal salt by addition of another component B.

The reaction of the phosphinic acid according to the invention with component A in process (2) is preferably carried out at a solids content of the salts of phosphinic acids according to the invention of from 0.1 to 70% by weight, preferably from 5 to 40% by weight.

The reaction in process (2) is preferably carried out at a temperature of from −20 to +500° C., particularly preferably from 70 to 160° C.

The ratio of component A to phosphorus (of the phosphinic acid according to the invention) in process (2) is preferably from 0.8 to 3 ion equivalents (mole per charge on the cation), particularly preferably from 1 to 2.

The molar ratio of solvent to phosphorus (of the phosphinic acid according to the invention) in process (2) is preferably from 2 to 1000, particularly preferably from 4 to 100.

A solvent system which is preferred according to the invention in process (2) has a dissociation constant pKa of from 10 to 30.

A component A which is preferred according to the invention in process (2) is a salt of an element of main group 1, preferably an alkali metal hydroxide, alkali metal oxide hydroxide, alkali metal hydroxide carbonate, alkali metal alkoxide, particularly preferably lithium hydroxide, sodium hydroxide, potassium hydroxide, sodium methoxide, sodium ethoxide, sodium n-propoxide, sodium i-propoxide, sodium n-butoxide, sodium i-butoxide, sodium tert-butoxide, sodium amylate, sodium glycolate.

A component A which is preferred according to the invention in process (2) is a salt of an element of main group 1, preferably an element of main group or transition group 2, preferably an alkaline earth metal hydroxide, alkaline earth metal oxide hydroxide, alkaline earth metal hydroxide carbonate, particularly preferably magnesium hydroxide (® Magnifin H5, Albermarle), hydrotalcite ($Mg_6Al_2(OH)_{15}CO_3$*$nH_2O$), dihydrotalcite, magnesium carbonate or magnesium calcium carbonate, calcium hydroxide, basic zinc carbonate, zinc hydroxide carbonate, basic zinc carbonate hydrate, zinc hydroxide or a mixed zinc oxide hydroxide (standard zinc oxide, e.g. from Grillo, activated zinc oxide, e.g. from Rheinchemie, zincite, calamine), zinc hydroxystannate.

A component A which is preferred according to the invention in process (2) is a salt of an element of main or transition group 3, preferably aluminum hydroxide, cerium hydroxide, lanthanum hydroxide, aluminum alkoxide, cerium alkoxide, lanthanum alkoxide, aluminum hydroxide or mixed aluminum oxide hydroxide, dihydroxyaluminum sodium carbonate $NaAl(OH)_2CO_3$ and/or a polyaluminum hydroxy compound which preferably has an aluminum content of from 9 to 40% by weight.

A component A which is preferred according to the invention in process (2) is a salt of an element of main or transition group 4, preferably zinc hydroxide, lead hydroxide, titanium oxide hydroxide, zirconium oxide hydroxide, tin alkoxide, titanium alkoxide, zirconium alkoxide.

Titanium alkoxides which are preferred according to the invention are titanium(IV) n-propoxide, (® Tilcom NPT, ® Vertec NPT), titanium(IV) n-butoxide, titanium chloride triisopropoxide, titanium(IV) ethoxide, titanium(IV) 2-ethylhexyloxide (® Tilcom EHT, ® Vertetec EHT).

A tin alkoxide which is preferred according to the invention is tin(IV) tertbutoxide.

A zinc alkoxide which is preferred according to the invention is zirconium(IV) tert-butoxide.

Components B which are preferred according to the invention in process (3) are borates, carbonates, hydroxocarbonates, hydroxocarbonate hydrates, mixed hydroxocarbonates, mixed hydroxocarbonate hydrates, phosphates, sulfates, sulfate hydrates, hydroxosulfate hydrates, mixed hydroxosulfate hydrates, oxysulfates, acetates, nitrates, fluorides, fluoride hydrates, chloride, chloride hydrates, oxychlorides, bromides, iodides, iodide hydrates, carboxylic acid derivatives and/or alkoxides of an element of main group 1, of main group or transition group 2, preferably Mg, Ca, Zn, of main group or transition group 3, preferably Al, Ce, La.

Components B which are preferred according to the invention in process (3) are aluminum chloride, aluminum nitrate, aluminum sulfate, titanium sulfate, zinc nitrate, zinc sulfate and zinc chloride.

The reaction in process (3) is preferably carried out in a stirred vessel, mixer and/or kneader.

The reaction in process (3) is preferably carried out with an energy input of from 0.083 to 1.65 $kW/m^3$, particularly preferably 0.33-1.65 $kW/m^3$.

The salts of phosphinic acids according to the invention are preferably separated off from the reaction mixture in process (3) by filtration and/or centrifugation.

The salts of phosphinic acids according to the invention are preferably separated off in process (3) by means of pressure filters, vacuum filters, stirred filters, pressure candle filters, axial plate filters, circular plate filters, centrifugal disc filters, chamber/frame filter presses, automatic chamber filter presses, vacuum drum cell filters, vacuum disc cell filters, vacuum internal cell filters, vacuum flat cell filters, rotary pressure filters, vacuum belt filters.

The filtration pressure in process (3) is preferably from 0.5 Pa to 6 MPa. The filtration temperature in process (3) is preferably from 0 to 400° C. The specific filtration throughput in process (3) is preferably from 10 to 200 $kg*h^{-1*m-2}$.

The residual moisture content of the filtercake in process (3) is preferably from 5 to 60%.

The salts of ethylenebis(hydroxyalkylphosphinic acid) or ethylenediphosphinic acid according to the invention obtained in process (3) are preferably separated off by means of solid bowl centrifuges such as overflow centrifuges, peeler centrifuges, chamber centrifuges, screw discharge centrifuges, plate centrifuges, tube centrifuges, screen centrifuges such as suspension and oscillatory centrifuges, screen screw centrifuges, screen peeler centrifuges or pusher centrifuges.

The acceleration ratio in process (3) is preferably from 300 to 15 000.

The suspension throughput in process (3) is preferably from 2 to 400 $m^3*h^{-1}$.

The solids throughput in process (3) is preferably from 5 to 80 $t*h^{-1}$.

The residual moisture content of the cake in process (3) is preferably from 5 to 60%.

The salts of phosphinic acids according to the invention are preferably dried in process (3).

Apparatuses which are, according to the invention, suitable for drying in process (3) are chamber dryers, channel dryers, belt dryers (air velocity=2-3 m/s), plate dryers (temperature: 20 to 400° C.), drum dryers (100-250° C. hot gas temperature), paddle dryers (50-300° C. temperature), flow dryers (10-60 m/s air velocity, 50-300° C. exhaust air temperature), fluidized-bed dryers (0.2-0.5 m/s air velocity, 50-300° C. exhaust air temperature), roller dryers, tube dryers (20 to 200° C. temperature), paddle dryers, vacuum drying ovens (20 to 300° C. temperature, 0.001-0.016 MPa pressure), vacuum roller dryers (20 to 300° C. temperature, 0.004-0.014 MPa pressure), vacuum paddle dryers (20 to 300° C. temperature, 0.003-0.02 MPa pressure), vacuum cone dryers (20 to 300° C. temperature, 0.003-0.02 MPa pressure).

The invention also provides a process (4) for the formation of inventive ethylenediphosphinic acid of the type H—P(O)(OH)—$CR^1R^2$—$CR^3R^4$—P(O)(OH)—H from inventive ethylenebis(hydroxyalkylphosphinic acid) of the type HO—$CR^5R^6$—P(O)(OX)—$CR^1R^2$—$CR^3R^4$—P(O)(OX)—$CR^5R^6$OH.

An embodiment according to the invention of process (4) is heating the inventive ethylenebis(hydroxyalkylphosphinic acid) of the type HO—$CR^5R^6$—P(O)(OX)—$CR^1R^2$—$CR^3R^4$—P(O)(OX)—$CR^5R^6$OH.

The preferred temperature for the formation process in process (4) is from 20 to 300° C., particularly preferably from 50 to 200° C.

The preferred pressure for the formation process in process (4) is from 10 to 100 000 000 Pa.

Preference is given to a molar ratio of protic acid to inventive ethylenebis(hydroxyalkylphosphinic acid) of the type HO—$CR^5R^6$—P(O)(OX)—$CR^1R^2$—$CR^3R^4$—P(O)(OX)—$CR^5R^6$OH in process (4) of from 100:1 to 1:100, particularly preferably from 10:1 to 1:10.

The protic acid is preferably removed in process (4). The removal is preferably effected by distillation, extraction and/or crystallization.

The preferred temperature for the removal of the protic acid in process (4) is from 20 to 300° C., particularly preferably from 50 to 200° C.

The preferred pressure for the removal of the protic acid in process (4) is from 10 to $10^8$ Pa.

According to the invention, the heating in process (4) is preferably carried out in the presence of a solvent.

The preferred temperature for separating off the solvent in process (4) is from 20 to 300° C., particularly preferably from 50 to 200° C.

The preferred pressure for separating of the solvent in process (4) is from 10 to $10^8$ Pa.

The ethylenebis(hydroxyalkylphosphinic acid) according to the invention is preferably used for preparing the ethylenediphosphonic acid with elimination of the end groups (this is possible as acids/alkali metal salts/Al salts, etc).

Here, preference is given to using the inventive phosphinic acid and/or salt thereof of the type

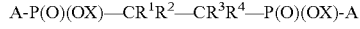

and derivatives thereof where $R^1$, $R^2$, $R^3$, $R^4$ are each H, $C_1$-$C_{20}$-alkyl, aryl (preferably phenyl) and/or aralkyl, A is $CR^1R^2$OH, X is H, alkali metal, Al, Zn, Ca, Mg, Ti, nitrogen base (preferably $NH_4$, ethylenediamine, melamine, etc) for preparing the inventive phosphinic acid and/or salt thereof of the type

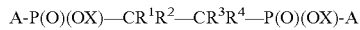

and derivatives thereof where $R^1$, $R^2$, $R^3$, $R^4$ are each H, $C_1$-$C_{20}$-alkyl, aryl (preferably phenyl) and/or aralkyl, A is H, X is H, alkali metal, Al, Zn, Ca, Mg, Ti, nitrogen base (preferably $NH_4$, ethylenediamine, melamine, etc).

Preference is given to using the inventive phosphinic acid and/or salt thereof for producing flame-retarded polymer molding compositions.

The flame-retarded polymer molding composition preferably contains from 0.5 to 45% by weight of inventive phosphinic acid and/or salt thereof, from 0.5 to 95% by weight of polymer or mixtures thereof, from 0.5 to 55% by weight of additives, from 0.5 to 55% by weight of filler or reinforcing materials, with the sum of the components being 100% by weight.

The flame-retarded polymer molding composition preferably contains from 10 to 40% by weight of inventive phosphinic acid and/or salt thereof, from 10 to 80% by weight of polymer or mixtures thereof, from 2 to 40% by weight of additives, from 2 to 40% by weight of filler or reinforcing materials, with the sum of the components being 100% by weight.

In a process for producing flame-retarded polymer molding compositions, the inventive phosphinic acid and/or salt thereof is mixed with the polymer pellets and possibly additives and compounded on a twin-screw extruder (ZSK 25 WLE, 14.5 kg/h, 200 rpm, L/D: 4) at temperatures of 170° C. (polystyrene), about 270° C. (PET, polyethylene terephthalate) from 230 to 260° C. (polybutylene terephthalate, PBT), 260° C. (PA6) or from 260 to 280° C. (PA 66). The homogenized polymer strand is taken off, cooled in a water bath, subsequently pelletized and dried to a residual moisture content of from 0.05 to 5% by weight, preferably from 0.1 to 1% by weight.

In a process for producing a flame-retarded polymer molding composition, 1000 parts by weight of dimethyl terephthalate and 720 parts by weight of ethylene glycol and from 35 to 700 parts by weight of a phosphinic acid according to the invention are polymerized. If desired, the polymerization can be carried out in the presence of zinc acetate. If desired, the flame-retarded polymer molding composition can be spun to produce fibers.

The polymer is preferably a thermoplastic or thermoset polymer.

The thermoplastic polymers are preferably polymers of monoolefins and diolefins, for example polypropylene, polyisobutylene, poly-1-butene, poly-4-methyl-1-pentene, polyisoprene or polybutadiene and also polymers of cycloolefins, e.g. of cyclopentene or norbornene; also polyethylene (which may, if appropriate, be crosslinked), e.g. high density polyethylene (HDPE), high molecular weight high density polyethylene (HMWHDPE), ultrahigh molecular weight high density polyethylene (UHMWHDPE), medium density polyethylene (MDPE), low density polyethylene (LDPE), linear low density polyethylene (LLDPE), branched low density polyethylene (BLDPE), and mixtures thereof.

The thermoplastic polymers are preferably copolymers of monoolefins and diolefins with one another or with other vinyl monomers, e.g. ethylene-propylene copolymers, linear low density polyethylene (LLDPE) and mixtures thereof with low density polyethylene (LDPE), propylene-1-butene copolymers, propylene-isobutylene copolymers, ethylene-1-butene copolymers, ethylene-hexene copolymers, ethylene methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene vinyl acetate copolymers and copolymers thereof with carbon monoxide, or ethylene-acrylic acid copolymers and salts thereof (ionomers), and also terpolymers of ethylene with propylene and a diene such as hexadiene, dicyclopentadiene or ethylidenenorbornene; also mixtures of such copolymers with one another, e.g. polypropylene/ethylene-propylene copolymers, LDPE/ethylene-vinyl acetate copolymers, LDPE/ethylene-acrylic acid copolymers, LLDPE/ethylene-vinyl acetate copolymers, LLDPE/ethylene-acrylic acid copolymers and alternating or random polyalkylene-carbon monoxide copolymers and mixtures thereof with other polymers such as polyamides.

The polymers are preferably hydrocarbon resins (e.g. $C_5$-$C_9$) including hydrogenated modifications thereof (e.g. tackifier resins) and mixtures of polyalkylenes and starch.

The thermoplastic polymers are preferably polystyrene, poly(p-methylstyrene) and/or poly(alpha-methylstyrene).

The thermoplastic polymers are preferably copolymers of styrene or alpha-methylstyrene with dienes or acrylic derivatives, e.g. styrene-butadiene, styrene-acrylonitrile, styrene-alkyl methacrylate, styrene-butadiene-alkyl acrylate or methacrylate, styrene-maleic anhydride, styrene-acrylonitrile-methyl acrylate; high-impact mixtures of styrene copolymers and another polymer, e.g. a polyacrylate, a diene polymer or an ethylene-propylene-diene terpolymer; and also block copolymers of styrene, e.g. styrene-butadiene-styrene, styrene-isoprene-styrene, styrene-ethylene/butylene-styrene or styrene-ethylene/propylene-styrene.

The thermoplastic polymers are preferably graft copolymers of styrene or alp ha-methylstyrene, e.g. styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, and also mixtures thereof, as are known as, for example, ABS, MBS, ASA or AES polymers.

The thermoplastic polymers are preferably halogen-containing polymers such as polychioroprene, chlorinated rubber, chlorinated and brominated copolymer of isobutylene-isoprene (halobutyl rubber), chlorinated or chlorosulfonated polyethylene, copolymers of ethylene and chlorinated ethylene, epichlorohydrin homopolymers and copolymers, in particular polymers of halogen-containing vinyl compounds, e.g. polyvinyl chloride, polyvinylidene chloride, polyvinyl fluoride, polyvinylidene fluoride; and also copolymers thereof, e.g. vinyl chloride-vinylidene chloride, vinyl chloride-vinylacetate or vinylidene chloride-vinyl acetate.

The thermoplastic polymers are preferably polymers derived from alpha, beta-unsaturated acids and derivatives thereof, e.g. polyacrylates and polymethacrylates, butyl acrylate-impact-modified polymethyl methacrylates, polyacrylamides and polyacrylonitriles and copolymers of the abovementioned monomers with one another or with other unsaturated monomers, e.g. acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

The thermoplastic polymers are preferably polymers derived from unsaturated alcohols and amines or acyl derivatives or acetals thereof, e.g. polyvinyl alcohol, polyvinyl acetate, stearate, benzoate, maleate, polyvinyl butyral, polyallyl phthalate, polyallyl melamine; and also copolymers thereof with olefins.

The thermoplastic polymers are preferably homopolymers and copolymers of cyclic ethers, e.g. polyalkylene glycols, polyethylene oxide, polypropylene oxide or copolymers thereof with bisglycidyl ethers.

The polymers are preferably thermoplastic polyacetals such as polyoxymethylene or polyoxymethylenes containing comonomers, e.g. ethylene oxide; polyacetals modified with thermoplastic polyurethanes, acrylates or MBS.

The thermoplastic polymers are preferably polyphenylene oxides and sulfides and mixtures thereof with styrene polymers or polyamides.

The thermoplastic polymers are preferably polyurethanes derived from polyethers, polyesters and polybutadienes having terminal hydroxyl groups and aliphatic or aromatic polyisocyanates, and also intermediates derived therefrom.

The thermoplastic polymers are preferably polyamides and copolyamides derived from diamines and dicarboxylic acids and/or from aminocarboxylic acids or the corresponding lactams, e.g. polyamide 4, polyamide 6 (® Akulon K122, DSM; ® Zytel 7301, from DuPont; ® Durethan B 29, from Bayer), polyamide 6/6 (® Zytel 101, from DuPont; ® Durethan A30, ® Durethan AKV, ® Durethan AM, from Bayer; ® Ultramid A3, from BASF) 6/10, 6/9, 6/12, 4/6, 12/12; polyamide 11, polyamide 12 (® Grillamid L20, from Ems Chemie), aromatic polyamides derived from m-xylene, diamine and adipic acid; polyamides prepared from hexamethylenediamine and isophthalic and/or terephthalic acid and, if appropriate, an elastomer as modifier, e.g. poly-2,4,4-trimethylhexamethyleneterephthalamide or poly-m-phenyleneisophthalamide; block copolymers of the abovementioned polyamides with polyolefins, olefin copolymers, ionomers or chemically bounded or grafted elastomers; or with polyethers, e.g. with polyethylene glycol, polypropylene glycol or polytetramethylene glycol; also polyamides or copolyamides modified with EPDM or ABS; and also polyamides which have been condensed during processing ("RIM polyamide systems").

The polymers are preferably polyureas, polyimides, polyamide imides, polyetherimides, polyesterimides, polyhydantoins and polybenzimidazoles.

The thermoplastic polymers are preferably polyesters derived from dicarboxylic acids and dialcohols and/or from hydroxycarboxylic acids or the corresponding lactones, e.g. polyethylene terephthalate, polybutylene terephthalate (® Celanex 2500, ® Celanex 2002, from Celanese; ® Ultradur, from BASF), poly-1,4-dimethylolcyclohexane terephthalate, polyhydroxybenzoates, and also block polyether esters derived from polyethers having hydroxyl end groups; also polyesters modified with polycarbonates or MBS.

The thermoplastic polymers are preferably polycarbonates and polyester carbonates, polysulfones, polyether sulfones and polyether ketones.

The polymers are preferably mixtures (polyblends) of the abovementioned polymers, e.g. PP/EPDM, polyamide/EPDM or ABS, PVC/EVA, PVC/ABS, PVC/MBS, PC/ABS, PBTP/ABS, PC/ASA, PC/PBT, PVC/CPE, PCV/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Preference is given to using the inventive phosphinic acid and/or salt thereof for producing flame-retardant polymer moldings, films, threads and fibers.

The flame-retarded polymer moldings, films, threads and fibers preferably contain from 0.5 to 45% by weight of inventive phosphinic acid and/or salt thereof, from 0.5 to 95% by weight of thermoplastic polymer or mixtures thereof.

The flame-retardant polymer moldings, films, threads and fibers preferably contain from 0.5 to 45% by weight of inventive phosphinic acid and/or salt thereof, from 0.5 to 95% by weight of thermoplastic polymer or mixtures thereof, from 0.5 to 55% by weight of additives, from 0.5 to 55% by weight of filler or reinforcing materials.

Finally, the invention also provides a process for producing flame-retarded polymer moldings, wherein flame-retarded polymer molding compositions according to the invention are processed by injection molding (e.g. injection-molding machine (model: Aarburg Allrounder) and pressing, foam injection molding, gas internal pressure injection molding, blow molding, tape casting, calendering, lamination or coating at relatively high temperatures to produce flame-retarded polymer moldings.

In the process for producing flame-retarded polymer moldings, the flame-retarded molding composition according to the invention is processed at melt temperatures according to the invention to produce polymer moldings.

Melt temperatures which are preferred according to the invention are from 200 to 250° C. in the case of polystyrene, from 200 to 300° C. in the case of polypropylene, from 250 to 290° C. in the case of polyethylene terephthalate (PET), from 230 to 270° C. in the case of polybutylene terephthalate (PBT), from 260 to 290° C. in the case of polyamide 6 (PA 6), from 260 to 290° C. in the case of polyamide 6.6 (PA 6.6) and from 280 to 320° C. in the case of polycarbonate.

A flame-resistant thermoset composition according to the invention comprises from 0.1 to 45% by weight of phosphinic acid according to the invention, from 40 to 90% by weight of unsaturated polyester, from 10 to 60% by weight of vinyl monomer.

The thermoset polymers are preferably unsaturated polyester resins derived from copolyesters of saturated and unsaturated dicarboxylic acids or anhydrides thereof with polyhydric alcohols and also vinyl compounds as crosslinkers. UP resins are cured by free-radical polymerization using initiators (e.g. peroxides) and accelerators.

Preferred unsaturated dicarboxylic acids and derivatives for preparing the polyesters are maleic anhydride and fumaric acid.

Preferred saturated dicarboxylic acids are phthalic acid, isophthalic acid, terephthalic acid, tetrahydrophthalic acid, adipic acid.

Preferred diols are 1,2-propanediol, ethylene glycol, diethylene glycol and neopentyl glycol, ethoxylated or propoxylated bisphenol A.

A preferred vinyl compound for crosslinking is styrene.

Preferred hardener systems are peroxides and metal coinitiators, e.g. hydroperoxides and cobalt octanoate and/or benzoyl peroxide and aromatic amines and/or UV sensitizers and photosensitizers, e.g. benzoin ethers.

Preferred hydroperoxides are di-tert-butyl peroxide, tert-butyl peroctoate, tert-butyl perpivalate, tert-butyl per-2-ethylhexanoate, tert-butyl permaleate, tert-butyl perisobutyrate, benzoyl peroxide, diacetyl peroxide, succinyl peroxide, p-chlorobenzoyl peroxide or dicyclohexyl peroxydicarbonate.

Preference is given to using initiators in amounts of from 0.1 to 20% by weight, preferably from 0.2 to 15% by weight, based on the mass of all comonomers.

Preferred metal coinitiators are cobalt, manganese, iron, vanadium, nickel or lead compounds. Preference is given to using metal coinitiators in amounts of from 0.05 to 1% by weight, based on the mass of all comonomers.

Preferred aromatic amines are dimethylaniline, dimethylamino-p-toluene, diethylaniline, phenyldiethanolamines.

A process for producing flame-retarded copolymers is carried out by copolymerizing (A) at least one ethylenically unsaturated dicarboxylic anhydride derived from at least one $C_4$-$C_8$-dicarboxylic acid, (B) at least one vinylaromatic compound and (C) polyol and then reacting the product with (D) phosphinic acid according to the invention.

A process for producing flame-retarded thermoset compositions is carried out by mixing a thermoset resin with a flame retardant component comprising phosphinic acid according to the invention and wet pressing the resulting mixture at pressures of from 3 to 10 bar and temperatures of from 20 to 60° C. (cold pressing).

Another process for producing flame-resistant thermoset compositions is carried out by mixing a thermoset resin with phosphinic acid according to the invention and wet pressing the resulting mixture at pressures of from 3 to 10 bar and temperatures of from 80 to 150° C. (warm or hot pressing).

The polymers are preferably crosslinked epoxy resins derived from aliphatic, cycloaliphatic, heterocyclic or aromatic glycidyl compounds, e.g. products of bisphenol A diglycidyl ethers, bisphenol F diglycidyl ethers, which are crosslinked by means of customary hardeners and/or accelerators.

Glycidyl compounds which can be used according to the invention are bisphenol A diglycidyl esters, bisphenol F diglycidyl esters, polyglycidyl esters of phenol-formaldehyde resins and cresol-formaldehyde resins, polyglycidyl esters of phthalic, isophthalic and terephthalic acid and of trimellitic acid, N-glycidyl compounds of aromatic amines and heterocyclic nitrogen bases and also diglycidyl and polyglycidyl compounds of polyhydric aliphatic alcohols.

Suitable hardeners are polyamines such as diethylenetriamine, triethylenetetramine, aminoethylpiperazine, isophoronediamine, polyamidoamine, diaminodiphenylmethane, diaminodiphenol sulfones, dicyandiamide.

Suitable hardeners are polybasic acids or anhydrides thereof, e.g. phthalic anhydride, maleic anhydride, tetrahydrophthalic anhydride, methyltetrahydrophthalic anhydride, hexahydrophthalic anhydride, methylhexahydrophthalic anhydride.

Suitable hardeners are phenols such as phenol Novolak resin, cresol Novolak resin, cyclopentadiene-phenol adduct resin, phenol-aralkyl resin, cresol-aralkyl resin, naphthol-aralkyl resin, bisphenol-modified phenol-aralkyl resin, phenol-trimethylolmethane resin, tetraphenylolethane resin, naphthol Novolak resin, naphthol-phenol cocondensate resin, naphthol-cresol cocondensate resin, bisphenol-modified phenolic resin and amino-triazine-modified phenolic resin.

These hardeners can be used either alone or in combination with one another.

Catalysts or accelerators according to the invention for crosslinking in polymerization are tertiary amines, benzyldimethylamine, N-alkylpyridines, imidazole, 1-methylimidazole, 2-methylimidazole, 2-ethyl-4-methyl-imidazole, 2-ethyl-4-methylimidazole, 2-phenylimidazole, 2-heptadecylimidazole, metal salts of organic acids, Lewis acids and amine complex salts.

Epoxy resins are suitable for the embedding of electric or electronic components and for steeping and impregnation processes. In electrical engineering, the epoxy resins used are predominantly provided with flame retardants and used for circuit boards and insulators.

The polymers are preferably crosslinked polymers derived from aldehydes and phenols, urea or melamine, e.g. phenol-formaldehyde, urea-formaldehyde and melamine-formaldehyde resins.

The polymers are preferably crosslinkable acrylic resins derived from substituted acrylic esters, e.g. from epoxy acrylates, urethane acrylates or polyester acrylates.

The polymers are preferably alkyd resins, polyester resins and acrylate resins crosslinked by means of melamine resins, urea resins, isocyanates, isocyanurates, polyisocyanates or epoxy resins.

A flame-retarded polyurethane molding composition can be produced by reacting from 0.1 to 50 parts by weight of phosphinic acid according to the invention with from 30 to 65 parts by weight of polyisocyanate and from 30 to 65 parts by weight of polyol.

In a process for producing a flame-retarded polyurethane molding composition, from 170 to 70 parts by weight, preferably from 130 to 80 parts by weight, of polyisocyanates according to the invention are reacted with 100 parts by weight of polyol according to the invention, from 0.1 to 50 parts by weight of phosphinic acid according to the invention and from 0.1 to 4 parts by weight, particularly preferably from 1 to 2 parts by weight, of catalyst according to the invention and, if desired, foamed by means of from 0.1 to 1.8 parts by weight, preferably from 0.3 to 1.6 parts by weight, of blowing agent.

Preferred polyols are alkene oxide adducts of ethylene glycol, 1,2-propanediol, bisphenol A, trimethylolpropane, glycerol, pentaerythritol, sorbitol, sugar, degraded starch, ethylenediamine, diaminotoluene and/or aniline, which serve as starter. The oxyalkylating agents which are preferred according to the invention preferably contain from 2 to 4 carbon atoms and are particularly preferably ethylene oxide and propylene oxide.

Preferred polyester polyols are obtained by polycondensation of a polyalcohol such as ethylene glycol, diethylene glycol, propylene glycol, 1,4-butanediol, 1,5-pentanediol, methylpentanediol, 1,6-hexanediol, trimethylolpropane, glycerol, pentaerythritol, diglycerol, glucose and/or sorbitol with a dibasic acid such as oxalic acid, malonic acid, succinic acid, tartaric acid, adipic acid, sebacic acid, maleic acid, fumaric acid, phthalic acid, terephthalic acid. These polyester polyols can be used either alone or in combination.

Suitable polyisocyanates are aromatic, alicyclic or aliphatic polyisocyanates having no fewer than two isocyanate groups and mixtures thereof. Preference is given to aromatic polyisocyanates such as tolylene diisocyanate, methylenedi(phenyl isocyanate), naphthylene diisocyanate, xylylene diisocyanate, tris(4-isocyanatophenyl)methane and polymethylenepolyphenylene diisocyanates; alicyclic polyisocyanates are methylenedi(phenyl isocyanate), tolylene diisocyanate; and aliphatic polyisocyanates are hexamethylene diisocyanate, isophorone diisocyanate, dimeryl diisocyanate, 1,1-methylenebis(4-isocyanatocyclohexane)-4,4'-diisocyanatodicyclohexylmethane isomer mixture, 1,4-cyclohexyl diisocyanate, (R)Desmodur grades (Bayer) and lysine diisocyanate and mixtures thereof.

Suitable polyisocyanates are modified products obtained by reaction of polyisocyanate with polyol, urea, carbodiimide and/or biuret.

Suitable catalysts are strong bases, alkali metal salts of carboxylic acids or aliphatic tertiary amines. Preference is given to quaternary ammonium hydroxides, alkali metal hydroxide or alkoxide, sodium or potassium acetate, potassium octoate, sodium benzoate, 1,4-diazabicyclo[2.2.2]-octane, N,N,N',N'-tetramethylhexamethylenediamine, N,N,N', N'-tetramethylpropylenediamine, N,N,N',N',N''-pentamethyldiethylenetriamine, N,N'-di-(C1-C2)-alkylpiperazine, trimethylaminoethylpiperazine, N,N-dimethylcyclohexylamine, N,N-dimethylbenzylamine, N-methylmorpholine, N-ethylmorpholine, trimethylamine, triethylamine, tributylamine, triethylenediamine, bis(dimethylaminoalkyl)piperazine, N,N,N',N'-tetramethylethylenediamine, N,N-diethylbenzylamine, bis(N,N-diethylaminoethyl) adipate, N,N,N',N'-tetramethyl-1,3-butanediamine, N,N-diethyl[beta]phenylethylamine, 1,2-dimethylimidazole, 2-methylimidazole etc.

The weight ratio of polyisocyanates to polyol is preferably 170:70, more preferably 130:80, based on 100 parts by weight of the polyol.

The weight ratio of catalyst is preferably from 0.1 to 4 parts by weight, particularly preferably from 1 to 2 parts by weight, per 100 parts by weight of the polyol.

Preferred blowing agents are water, hydrocarbon, chlorofluorocarbon, fluorinated hydrocarbon, etc.

The amount of any blowing agent used is from 0.1 to 1.8 parts by weight, preferably from 0.3 to 1.6 parts by weight, preferably from 0.8 to 1.6 parts by weight, per 100 parts by weight of the polyol.

The decomposition temperature is determined by standard thermo-gravimetric methods. The decomposition temperature is defined here as the temperature at which a weight loss of 2% occurs.

Chemicals Used

1-Hydroxy-1-methylethylphosphinic acid, $H-P(O)(OH)C(CH_3)_2OH$

Wako V 65 B: 2,2'-Azobis-2,4-dimethylvaleronitrile

Waco V50: 2,2'-Azobis-2-amidinopropane hydrochloride

VAZO 52: 2,2'-Azobisisopropylbutyronitrile

VAZO 67: 2,2'-Azobismethylbutyronitrile

VAZO 64: AIBN 2,2'-azobisisobutyronitrile

EBHA: Ethylenebis(1-hydroxy-1-methylethylphosphinic acid), $HO-C(CH_3)_2-P(O)(OH)-CH_2-CH_2-P(O)(OH)-C(CH_3)_2-OH$ EBHNa: Disodium ethylenebis(1-hydroxy-1-methylethylphosphinate), $HO-C(CH_3)_2-P(O)(ONa)-CH_2-CH_2-P(O)(ONa)-C(CH_3)_2-OH$ EBHAl: Aluminum ethylenebis(1-hydroxy-1-methylethylphosphinate), $HO-C(CH_3)_2-P(O)(OAl_{1/3})-CH_2-CH_2-P(O)(OAl_{1/3})-C(CH_3)_2OH$ EBHZn: Zinc ethylenebis(1-hydroxy-1-methylethylphosphinate), $HO-C(CH_3)_2-P(O)(OZn_{1/2})-CH_2-CH_2-P(O)(OAl_{1/2})-C(CH_3)_2OH$ EBHCa: Calcium ethylenebis(1-hydroxy-1-methylethylphosphinate), $HO-C(CH_3)_2-P(O)(OCa_{1/2})-CH_2-CH_2-P(O)(OCa_{1/2})-C(CH_3)_2-OH$ EBHMg: Magnesium ethylenebis(1-hydroxy-1-methylethylphosphinate), $HO-C(CH_3)_2-P(O)(OMg_{1/2})-CH_2-CH_2-P(O)(OMg_{1/2})-C(CH_3)_2-OH$ EBHFe: Iron ethylenebis(1-hydroxy-1-methylethylphosphinate), $HO-C(CH_3)_2-P(O)(OFe_{1/3})-CH_2-CH_2-P(O)(OFe_{1/3})-C(CH_3)_2-OH$ EBPA: Ethylenebisphosphinic acid, $H-P(O)(OH)-CH_2-CH_2-P(O)(OH)-H$ EBPNa: Disodium ethylenebisphosphinate, $H-P(O)(ONa)-CH_2-CH_2-P(O)(ONa)-H$ EBPAl: Aluminum ethylenebisphosphinate, $H-P(O)(OAl_{1/3})-CH_2-CH_2-P(O)(OAl_{1/3})-H$ EBPZn: Zinc ethylenebisphosphinate, $H-P(O)(OZn_{1/2})-CH_2-CH_2-P(O)(OZn_{1/2})-H$ EBPCa: Calcium ethylenebisphosphinate, $H-P(O)(OCa_{1/2})-CH_2-CH_2-P(O)(OCa_{1/2})-H$ EBPFe: Iron ethylenebisphosphinate, H—P(O)(OFe$_{1/3}$)—CH$_2$—CH$_2$—P(O)(OFe$_{1/3}$)—H
EBPMel: Melamine ethylenebisphosphinate, H—P(O)(OC$_3$H$_6$N$_6$)—CH$_2$—CH$_2$—P(O)(OC$_3$H$_6$N$_6$)—H
Polystyrene: Polystyrol 143 E, from BASF
PA 6.6: ® Ultramid A3, from BASF
MPP: ® Melapur 200/70, from Ciba SC
Glass fibers 1: VPPG 3540, from PPG Industries, Inc
Glass fibers 2: ® Vetrotex EC 10983, from Saint Gobain

EXAMPLES

Preparation of Concentrated Hypophosphorous Acid (HPA, H$_3$PO$_2$)

Concentrated HPA can be prepared according to the prior art.
Commercially available 50% aqueous hypophosphorous acid is concentrated by evaporation to constant weight on a rotary evaporator under a water pump vacuum and a temperature which does not exceed 40° C.

1-Hydroxy-1-methylethylphosphinic acid (HMPPA)

1-Hydroxy-1-methylethylphosphinic acid is prepared according to the prior art from concentrated HPA and isolated as a pale yellow oil to white resin in a yield of 96%.

Method of Preparing ethylenebis(1-hydroxy-1-methylethylphosphinic acid)

HMPPA and amyl alcohol were placed in a two liter five-neck flask provided with stirrer, thermometer, low-temperature condenser, initiator metering, frit for introduction of acetylene and blanketing with nitrogen and homogenized. The reaction mixture was heated. The stirrer speed was 460 rpm. After the reaction temperature had been reached, the initiator was metered in as 10% strength solution in the appropriate solvent by means of a pump. Acetylene was introduced at 5-6 l/h. The product precipitates during the reaction and, after the reaction is complete, is filtered off on a suction filter and washed twice with acetone. The powder was dried at 120° C. in a drying oven. Typical purity: 93.6% ($^{31}$P-NMR). The product is X-ray crystalline. The following reflections (CuK$_{alpha\ 1}$ radiation 1.54056 Ang) are observed: rel. intensity/d: 20.2, 7.78620; 62.9, 5.63264; 100.0, 5.33438; 27.5, 4.91046; 47.2%, 4.49822 Ang. The hydroxyl group number is 290 mg KOH/g.
The product can, if desired, be digested with ethanol (25% strength dispersion) to purify it further. The yields in this step are 80-90% and lead to purities of about 99.2% ($^{31}$P-NMR).

Example 1

345 g of 1-hydroxy-1-methylethylphosphinic acid and 29.8 g of Wako V65 B initiator in a total of 803 g of amyl alcohol at 80° C. for 11 hours give 210 g of product.

Example 2

345 g of 1-hydroxy-1-methylethylphosphinic acid and 18.3 g of VAZO 52 initiator in a total of 803 g of amyl alcohol at 50° C. for 11 hours give 141 g of product.

Example 3

345 g of 1-hydroxy-1-methylethylphosphinic acid and 19.7 g of AIBN initiator in a total of 803 g of amyl alcohol at 120° C. for 8 hours give 240 g of product.

Example 4

345 g of 1-hydroxy-1-methylethylphosphinic acid and 6.9 g of Wako V65 B initiator in a total of 803 g of amyl alcohol at 80° C. for 32 hours give 187 g of product.

Example 5

345 g of 1-hydroxy-1-methylethylphosphinic acid and 29.8 g of Wako V65 B initiator in a total of 350 g of amyl alcohol at 80° C. for 11 hours give 259 g of product.

Example 6

Disodium ethylenebis(1-hydroxy-1-methylethylphosphinate)

141 g of demineralized water are placed in a 1 l glass beaker and firstly 40 g of NaOH pellets and then 137.1 g of EBHA are carefully added while stirring. 318 g of a 50% strength by weight solution of EBHNa are obtained.

General Method of Preparing ethylenebis(1-hydroxy-1-methylethylphosphinate) Salts and Ethylenebisphosphinate Salts Either the demineralized water is placed in a two liter or four liter six-neck flask (provided with stirrer, thermometer, stopper, inlet tube and reflux condenser) and the metal salt is dissolved with heating to the precipitation temperature or the finished metal salt solution is placed in the flask and heated to the precipitation temperature. The calculated amount of EBHNa solution is pumped in via an inlet tube by means of a pump over the prescribed time. The preselected precipitation temperature is maintained and the mixture is stirred at a preselected stirrer speed. The solid product is filtered off hot on a suction filter, then dispersed by means of demineralized water at 90° C. (five times the amount of the theoretical yield) and again filtered off hot on a suction filter. The solid is dried at 100° C. and 30 mbar in a drying oven for 15 hours.

Example 7

Aluminum ethylenebis(1-hydroxy-1-methylethylphosphinate)

Using the general method for preparing the metal ethylenebis(1-hydroxy-1-methylethylphosphinates), 318 g of EBHNa solution are reacted with 209 g of aluminum sulfate solution at 90° C. and 750 rpm stirrer speed for 2 hours. 132 g of solid product are obtained. The product is X-ray crystalline. The following reflections (CuK$_{alpha\ 1}$ radiation 1.54056 Ang) are observed: rel. intensity/d: 65.6, 11.03554; 100.0, 10.55511; 30.2, 8.91804; 33.4%, 8.74638 Ang. The analytical data are shown in table 2.

Example 8

Zinc ethylenebis(1-hydroxy-1-methylethylphosphinate)

Using the general method for preparing the metal ethylenebis(1-hydroxy-1-methylethylphosphinates), 318 g of EBHNa solution are reacted with 144 g of zinc sulfate heptahydrate dissolved in 1240 g of demineralized water at 90° C. and 250 rpm stirrer speed for 2 hours. 135 g of solid product are obtained. The product is X-ray crystalline. The following reflections (CuK$_{alpha\ 1}$ radiation 1.54056 Ang) are observed: rel. intensity/d: 100.0, 11.09087; 35.7, 10.67607; 29.4, 5.26978; 40.3%, 4.91046 Ang. The analytical data are shown in table 2.

Example 9

Magnesium ethylenebis(1-hydroxy-1-methylethylphosphinate)

Using the general method for preparing the metal ethylenebis(1-hydroxy-1-methylethylphosphinates), 318 g of EBHNa solution are reacted with 102 g of magnesium chloride hexahydrate dissolved in 568 g of demineralized water at 50° C. and 750 rpm stirrer speed for 2 hours. 111 g of solid product are obtained. The product is X-ray crystalline. The following reflections (CuK$_{alpha\ 1}$ radiation 1.54056 Ang) are observed: rel. intensity/d: 100.0%, 11.23166 Ang. The analytical data are shown in table 2.

Example 10

Iron ethylenebis(1-hydroxy-1-methylethylphosphinate)

Using the general method for preparing the metal ethylenebis(1-hydroxy-1-methylethylphosphinates), 318 g of EBHNa solution are reacted with 67 g of iron sulfate dissolved in 2710 g of demineralized water at 90° C. and 750 rpm stirrer speed for 8 hours. 139 g of solid product are obtained. The analytical data are shown in table 2.

Example 11

Method of Preparing Ethylenebisphosphinic Acid by Elimination of Acetone from ethylenebis(1-hydroxy-1-methylethylphosphinic acid)

274 g of EBHA are weighed into a four-neck flask provided with distillation rectangle, dripping funnel and thermometer and admixed with 4 mol of hydrochloric acid (37% strength). The apparatus is made inert by means of nitrogen. The mixture is heated to the boiling point of the hydrochloric acid on an oil bath and the solution is boiled under reflux temperature (at the top: 105-108° C.). The temperature at the top decreases with time due to the elimination of acetone. Distillate is drained off every now and again until the temperature at the top remains constant at 108° C. (constantly replenished with 37% strength hydrochloric acid by means of a dropping funnel). When the boiling temperature is constant, the remaining hydrochloric acid is distilled off at 1 mbar and max. 110° C. on a rotary evaporator.

Example 12

Disodium ethylenebisphosphinate 83 g of demineralized water are placed in a 1 l glass beaker while stirring and firstly 40 g of NaOH pellets and then 79 g of EBPA are added carefully. 202 g of a 50% strength by weight solution of EBPNa are obtained.

Example 13

Aluminum ethylenebisphosphinate

Using the general method for preparing the metal ethylenebisphosphinates, 202 g of EBPNa solution are reacted with 209 g of aluminum sulfate solution at 90° C. and 750 rpm stirrer speed for 2 hours. 71 g of solid product are obtained. The analytical data are shown in table 3.

Example 14

Zinc ethylenebisphosphinate

Using the general method for preparing the metal ethylenebisphosphinates, 202 g of EBPNa solution are reacted with 144 g of zinc sulfate heptahydrate dissolved in 770 g of demineralized water at 100° C. and 1500 rpm stirrer speed for 1 hour. 95 g of solid product are obtained. The product is X-ray crystalline. The following reflections (CUK$_{alpha\ 1}$ radiation 1.54056 Ang) are observed: rel. intensity/d: 39.2, 7.82398; 37.2, 6.52943; 100.0, 3.90381; 63.3%, 3.22809 Ang. The analytical data are shown in table 3.

Example 15

Calcium ethylenebisphosphinate

Using the general method for preparing the metal ethylenebisphosphinates, 202 g of EBPNa solution are reacted with 74 g of calcium chloride dihydrate dissolved in 380 g of demineralized water at 90° C. and 750 rpm stirrer speed for 2 hours. 58 g of solid product are obtained. The analytical data are shown in table 3.

Example 16

Iron ethylenebisphosphinate

Using the general method for preparing the metal ethylenebisphosphinates, 202 g of EBPNa solution are reacted with 67 g of iron sulfate dissolved in 2720 g of demineralized water at 90° C. and 750 rpm stirrer speed for 2 hours. 90 g of solid product are obtained. The analytical data are shown in table 3.

Example 17

Dimelamine ethylenebisphosphinate 79 g of EBPA and 126 g of melamine are dissolved in hot ethylene glycol. On cooling 148 g of solid product precipitates. The product is X-ray crystalline. The following reflections (CuK$_{alpha\ 1}$ radiation 1.54056 Ang) are observed: rel. intensity/d: 39.0, 5.71392; 40.2, 3.95093; 100.0%, 3.43265 Ang. The analytical data are shown in table 3.

Example 18

Comparison

Using the general method, a mixture of 70% by weight of polystyrene and 30% by weight of calcium hypophosphite is compounded at 170° C. on a twin-screw extruder to give a polymer molding composition. Ignition occurs during processing as a result of decomposition of the flame retardant.

Example 19

Using the general method, a mixture of 70% by weight of polystyrene and 30% by weight of product from example 12 is compounded at 170° C. on a twin-screw extruder to give a polymer molding composition. After drying, the molding compositions are processed at 200-250° C. on an injection molding machine to produce polymer moldings and a UL-94 classification of V-0 is determined.

Example 20

Using the general method, a mixture of 70% by weight of polystyrene and 30% by weight of product from example 13 is compounded at 170° C. on a twin-screw extruder to give a polymer molding composition. After drying, the molding compositions are processed at 200-250° C. on an injection molding machine to produce polymer moldings and a UL-94 classification of V-0 is determined.

Example 21

Using the general method, a mixture of 70% by weight of polystyrene and 30% by weight of product from example 14 are compounded at 170° C. on a twin-screw extruder to give a flame-retarded polymer molding composition. After drying, the flame-retarded molding composition is processed at 200-250° C. on an injection molding machine to produce flame-retarded polymer moldings and a UL-94 classification of V-0 is determined.

Example 22

Using the general method, a mixture of 70% by weight of polystyrene and 30% by weight of product from example 15 are compounded at 170° C. on a twin-screw extruder to give a flame-retarded polymer molding composition. After drying, the flame-retarded molding composition is processed at 200-250° C. on an injection molding machine to produce flame-retarded polymer moldings and a UL-94 classification of V-0 is determined.

Example 23

Using the general method, a mixture of 50% by weight of PA 6.6, 12.5% by weight of product from example 12, 12.5% by weight of MPP and 25% by weight of glass fibers are compounded at 260-280° C. on a twin-screw extruder to give a flame-retarded polymer molding composition. After drying, the flame-retarded molding composition is processed at 260-290° C. on an injection molding machine to produce flame-retarded polymer moldings and a UL-94 classification of V-1 is determined.

Example 24

Using the general method, a mixture of 50% by weight of PBT, 12.5% by weight of product from example 13, 12.5% by weight of MPP and 25% by weight of glass fibers are compounded at 230-260° C. on a twin-screw extruder to give a flame-retarded polymer molding composition. After drying, the flame-retarded molding composition is processed at 230-270° C. on an injection molding machine to produce flame-retarded polymer moldings and a UL-94 classification of V-1 is determined.

Example 25

Comparison

An adhesive composition is produced from 82% of Airflex 920 (Air Products and Chemicals Inc), 1% of Tego antifoam (East Falls Corp.), 15% of AP 422 (Clariant GmbH) and 2% of Alcogum 296W (ALCO Chemical). 100 g of this composition are weighed into a 250 ml wide-neck screw-top bottle and stored at 60° C. for 8 hours. The gas space after storage was examined by means of formaldehyde test strips from Dräger Sicherheitstechnik GmbH (type 0.2/a). After pumping ten times, a formaldehyde concentration of greater than 50 ppm is read off.

Example 26

An adhesive composition is produced from 80% of Airflex 920 (Air Products and Chemicals Inc), 1% of Tego antifoam (East Falls Corp.), 15% of AP 422 (Clariant GmbH), 2% of Alcogum 296W (ALCO Chemical) and 2% of the product from example 11. The product is tested as described in example 25. A formaldehyde concentration of about 10 ppm is read off. The adhesive is particularly suitable for building applications.

TABLE 1

Preparation of ethylenebis(1-hydroxy-2-methylethylphosphinic acid)

| Example | HPA adduct g | Initiator Type | g | Solvent Type | g | Actylene g | T °C. | t h | Product g | % | DT °C., 2% WL | 31P-NMR ppm |
|---|---|---|---|---|---|---|---|---|---|---|---|---|
| 1 | 345 | Wako V65 B | 29.8 | AmOH | 803 | 64 | 80 | 11 | 210 | 55 | 167 | 54.8 |
| 2 | 345 | VAZO 52 | 18.3 | AmOH | 803 | 64 | 50 | 11 | 141 | 37 | | |
| 3 | 345 | AIBN | 19.7 | OctOH | 803 | 64 | 120 | 8 | 240 | 63 | | |
| 4 | 345 | Wako V65 B | 6.9 | AmOH | 803 | 64 | 80 | 32 | 187 | 49 | | |
| 5 | 345 | Wako V65 B | 29.8 | AmOH | 350 | 64 | 80 | 11 | 259 | 68 | | |

WL = Weight loss

DT = Decomposition temperature

TABLE 2

Preparation of ethylenebis(1-hydroxy-1-methyethylphosphinate) salts

| Example | Starting material A | g | Starting material B | g | Solvent | g | t h | T °C. | Stirrer speed rpm | Product g | DT °C. 2% WL | 31P-NMR ppm | P content exp % | th % |
|---|---|---|---|---|---|---|---|---|---|---|---|---|---|---|
| 6 | EBHA | 137 | NaOH | 40 | H₂O | 141 | 0.5 | 30 | 300 | 318 | — | 46 | — | — |
| 7 | EBHNa | 318 | Al₂(SO₄)₃ soln 4.3% Al | 209 | H₂O | 0 | 2 | 90 | 750 | 132 | 248 | 46 | 20.6 | 21.4 |
| 8 | EBHNa | 318 | ZnSO₄*7aq | 144 | H₂O | 1240 | 2 | 90 | 250 | 135 | 283 | 46 | 17.9 | 18.4 |
| 9 | EBHNa | 318 | MgCl₂*6aq | 102 | H₂O | 568 | 2 | 50 | 750 | 111 | 260 | 46 | 19.8 | 20.9 |
| 10 | EBHNa | 318 | Fe₂(SO₄)₃ | 67 | H₂O | 2710 | 8 | 90 | 750 | 139 | 262 | 46 | 19.5 | 20 |

TABLE 3

Preparation of ethylenebisphosphinate salts

| Example | Starting material A | g | Starting material B | g | Solvent | g | t h | T °C. | Stirrer speed rpm | Product g | DT °C. 2% WL | 31P-NMR ppm | P content exp % | th % |
|---|---|---|---|---|---|---|---|---|---|---|---|---|---|---|
| 12 | EBPA | 79 | NaOH | 40 | H₂O | 83 | 0.5 | 30 | 300 | 202 | — | 31 | — | — |
| 13 | EBPNa | 202 | Al₂(SO₄)₃ soln 4.3% Al | 209 | H₂O | 0 | 2 | 90 | 750 | 71 | >600 | 31 | 33.2 | 35.6 |
| 14 | EBPNa | 202 | ZnSO₄*7aq | 144 | H₂O | 770 | 1 | 100 | 1500 | 95 | >1000 | 31 | 27.7 | 28.0 |
| 15 | EBPNa | 202 | CaCl₂*2aq | 74 | H₂O | 380 | 2 | 90 | 750 | 58 | >600 | 31 | 30.0 | 31.6 |
| 16 | EBPNa | 202 | Fe₂(SO₄)₃ | 67 | H₂O | 2720 | 2 | 90 | 750 | 90 | >600 | 31 | 29.9 | 32.1 |
| 17 | EBPA | 79 | Melamine | 126 | Ethylene glycol | 3900 | 2 | 100 | 750 | 148 | 279 | 31 | 14.9 | 15.1 |

TABLE 4

Flame-retarded polymer molding compositions and flame resistance tests on flame-retarded polymer moldings

| | | Examples | | | | |
|---|---|---|---|---|---|---|
| | | 18 | 19 | 20 | 21 | 22 |
| Polystyrene | [% by weight] | 70 | 70 | 70 | 70 | 70 |
| Calcium hypophosphite | [% by weight] | 30 | | | | |
| Product from example 13 | [% by weight] | | 30 | | | |
| Product from example 14 | [% by weight] | | | 30 | | |
| Product from example 15 | [% by weight] | | | | 30 | |
| Product from example 16 | [% by weight] | | | | | 30 |
| UL-94 classification (1.5 mm) | | Ignition during processing | V-0 | V-0 | V-0 | V-0 |

TABLE 5

Flame-retarded polymer molding compositions and flame resistance tests on flame-retarded polymer moldings

| | Examples | |
|---|---|---|
| | 23 [% by weight] | 23 [% by weight] |
| PA 6.6 | 50 | |
| PBT | | 50 |
| Glass fibers 1 | 25 | |
| Glass fibers 2 | | 25 |
| Product from example 13 | 12.5 | |
| Product from example 14 | | 12.5 |
| MPP | 12.5 | — |
| MC | — | 12.5 |
| UL-94 class | V-1 | V-1 |

The invention claimed is:

1. An ethylenebis(hydroxyalkylphosphinic acid) or salt thereof having the formula (I):

A-P(O)(OX)—CR¹R²—CR³R⁴P(O)(OX)-A    (I)

wherein:

A is CR⁵R⁶—OH;

each $R^1$, $R^2$, $R^3$, $R^4$, $R^5$, and $R^6$ is independently selected from the group consisting of H, $C_1$-$C_{20}$-alkyl, $C_6$-$C_{20}$-aryl, and $C_6$-$C_{20}$-aralkyl, so long as at least one of $R^1$ and $R^2$ and at least one of $R^3$ and $R^4$ is H; and X is selected from the group consisting of H, an alkali metal, an element of main or transition group 2, an element of main or transition group 3, an element of main or transition group 4, an element of main or transition group 5, an element of transition group 6, an element of transition group 7, an element of transition group 8, and a nitrogen base.

2. The ethylenebis(hydroxyalkylphosphinic acid) or salt thereof as claimed in claim 1, wherein each $R^1$, $R^2$, $R^3$, $R^4$, $R^5$, and $R^6$ is independently selected from the group consisting of H, methyl, ethyl, n-propyl, i-propyl, n-butyl, tert-butyl, n-pentyl, and phenyl, so long as at least one of $R^1$ and $R^2$ and at least one of $R^3$ and $R^4$ is H.

3. The ethylenebis(hydroxyalkylphosphinic acid) or salt thereof as claimed in claim 1, wherein the ethylenebis(hydroxyalkylphosphinic acid) or salt thereof is capable of being implemented as: a flame retardant for clear coatings and intumescent coatings; a flame retardant for wood and cellulose-containing products; and a reactive or nonreactive flame retardant for polymers.

4. The ethylenebis(hydroxyalkylphosphinic acid) or salt thereof as claimed in claim 1, wherein the ethylenebis(hydroxyalkylphosphinic acid) or salt thereof is capable of being implemented as: a binder for foundry compositions and mold sands; a crosslinker or accelerator in the curing of epoxy resins, polyurethanes and unsaturated polyester resins; a polymer stabilizer; a light stabilizer; a free-radical scavenger or heat stabilizer for woven cotton fabrics, polymer fibers, and plastics; a crop protection agent; a plant growth regulator; an herbicide, pesticide, or fungicide; a sequestering agent in mineral oil recovery and in metal treatment agents; a mineral oil additive; a corrosion inhibitor in laundry detergent and cleaner applications; a free-radical scavenger in photosensitive layers; and an aldehyde scavenger and a formaldehyde scavenger in adhesives or moldings.

5. A flame-retarded thermoplastic polymer molding composition comprising: the ethylenebis(hydroxyalkylphosphinic acid) or salt thereof as claimed in claim 1; and a thermoplastic polymer or mixtures thereof; wherein the ethylenebis(hydroxyalkylphosphinic acid) or salt thereof is provided an amount of from 0.5 to 45% by weight, based on the overall composition.

6. A flame-retarded thermoset composition comprising: the ethylenebis(hydroxyalkylphosphinic acid) or salt thereof as claimed in claim 1; unsaturated polyesters; and vinyl monomers; wherein the ethylenebis(hydroxyalkylphosphinic acid) or salt thereof is provided an amount of from 0.1 to 45% by weight, based on the overall composition.

7. A flame-resistant epoxy resin comprising: the ethylenebis(hydroxyalkylphosphinic acid) or salt thereof as claimed in claim 1; an epoxy resin; and a hardener; wherein the ethylenebis(hydroxyalkylphosphinic acid) or salt thereof is provided an amount of from 0.5 to 50% by weight, based on the overall composition.

8. A process for preparing an ethylenebis (hydroxyalkylphosphinic acid) or salt thereof having the formula (I)

A-P(O)(OX)—$CR^1R^2$—$CR^3R^4$—P(O)(OX)-A    (I)

wherein:
A is $CR^5R^6$—OH;
$R^1$, $R^2$, $R^3$, and $R^4$ are H;
$R^5$ and $R^6$ are independently selected from the group consisting of H, $C_1$-$C_{20}$-alkyl, $C_6$-$C_{20}$-aryl, and $C_6$-$C_{20}$-aralkyl; and
X is H or an alkali metal;
said process comprising the steps of:
a) reacting acetylene with a monophosphinic acid adduct of the formula (II)

H—P(O)(OX)-A    (II); and b) optionally separating the resulting ethylenebis(hydroxyalkylphosphinic acid) or salt thereof from reaction by-products.

9. A process for preparing a salt of ethylenebis (hydroxyalkylphosphinic acid) of the type

A-P(O)(OX)-$CR^1R^2$—$CR^3R^4$—P(O)(OX)-A wherein:
A is $CR^5R^6$—OH;
each $R^1$, $R^2$, $R^3$, $R^4$, $R^5$, and $R^6$ is independently selected from the group consisting of H, $C_1$-$C_{20}$-alkyl, $C_6$-$C_{20}$-aryl, and $C_6$-$C_{20}$-aralkyl, so long as at least one of $R^1$ and $R^2$ and at least one of $R^3$ and $R^4$ is H; and
X is selected from the group consisting of an alkali metal, an element of main group or transition group 2, an element of main or transition group 3, an element of main or transition group 4, an element of main or transition group 5, an element of transition group 6, an element of transition group 7, an element of transition group 8, and a nitrogen base;
said process comprising the step of reacting a reactant I with an ethylenebis (hydroxyalkylphosphinic acid) in a solvent system;
wherein said ethylenebis(hydroxyalkylphosphinic acid) is of the type

A-P(O)(OX)-$CR^1R^2$—$CR^3R^4$—P(O)(OX)-A wherein:
A is $CR^5R^6$—OH;
each $R^1$, $R^2$, $R^3$, $R^4$, $R^5$, and $R^6$ is independently selected from the group consisting of H, $C_1$-$C_{20}$-alkyl, $C_6$-$C_{20}$-aryl, and $C_6$-$C_{20}$-aralkyl, so long as at least one of $R^1$ and $R^2$ and at least one of $R^3$ and $R^4$ is H; and
X is H; and
wherein reactant I is selected from the group consisting of a compound of an alkali metal, a compound of an element of main or transition group 2, a compound of an element of main or transition group 3, a compound of an element of main or transition group 4, a compound of an element of main or transition group 5, a compound of an element of transition group 6, a compound of an element of transition group 7, a compound of an element of transition group 8, and a nitrogen base.

10. A process for preparing a salt of ethylenebis (hydroxyalkylphosphinic acid) of the type

A-P(O)(OX)-$CR^1R^2$—$CR^3R^4$—P(O)(OX)-A wherein:
A is $CR^5R^6$—OH;
each $R^1$, $R^2$, $R^3$, $R^4$, $R^5$, and $R^6$ is independently selected from the group consisting of H, $C_1$-$C_{20}$-alkyl, $C_6$-$C_{20}$-aryl, and $C_6$-$C_{20}$-aralkyl, so long as at least one of $R^1$ and $R^2$ and at least one of $R^3$ and $R^4$ is H; and
X is selected from the group consisting of an element of main group or transition group 2, an element of main or transition group 3, an element of main or transition group 4, an element of main or transition group 5, an element of transition group 6, an element of transition group 7, an element of transition group 8, and a nitrogen base;
said process comprising the step of reacting a reactant II with a salt of an ethylenebis (hydroxyalkylphosphinic acid) in a solvent system;
wherein said salt of an ethylenebis(hydroxyalkylphosphinic acid) is of the type

A-P(O)(OX)-$CR^1R^2$—$CR^3R^4$—P(O)(OX)-A wherein:
A is $CR^5R^6$—OH;
each $R^1$, $R^2$, $R^3$, $R^4$, $R^5$, and $R^6$ is independently selected from the group consisting of H, $C_1$-$C_{20}$-alkyl, $C_6$-$C_{20}$-aryl, and $C_6$-$C_{20}$-aralkyl, so long as at least one of $R^1$ and $R^2$ and at least one of $R^3$ and $R^4$ is H; and X is an alkali metal; and
wherein reactant II is selected from the group consisting of a compound of an element of main or transition group 2, a compound of an element of main or transition group 3, a compound of an element of main or transition group 4, a compound of an element of main or transition group 5, a compound of an element of transition group 6, a compound of an element of transition group 7, a compound of an element of transition group 8, and a nitrogen base.

11. The process as claimed in claim 10, wherein reactant II is selected from the group consisting of a borate, carbonate, hydroxocarbonate, hydroxocarbonate hydrate, mixed hydroxocarbonate, mixed hydroxocarbonate hydrate, phosphate, sulfate, sulfate hydrate, hydroxosulfate hydrate, mixed hydroxosulfate hydrate, oxysulfate, acetate, nitrate, fluoride, fluoride hydrate, chloride, chloride hydrate, oxychloride, bromide, iodide, iodide hydrate, carboxylic acid derivative, alkoxide, and mixtures thereof.

* * * * *